(12) United States Patent
Ariessohn et al.

(10) Patent No.: US 7,875,095 B2
(45) Date of Patent: Jan. 25, 2011

(54) SKIMMER FOR CONCENTRATING AN AEROSOL

(75) Inventors: Peter C Ariessohn, Seattle, WA (US); Igor V Novosselov, Seattle, WA (US)

(73) Assignee: Enertechnix, Inc, Maple Valley, WA (US)

( * ) Notice: Subject to any disclaimer, the term of this patent is extended or adjusted under 35 U.S.C. 154(b) by 359 days.

(21) Appl. No.: 12/125,458

(22) Filed: May 22, 2008

(65) Prior Publication Data

US 2009/0288475 A1    Nov. 26, 2009

(51) Int. Cl.
*B01D 45/00* (2006.01)
(52) U.S. Cl. .................... 55/434; 73/28.06; 73/863.22
(58) Field of Classification Search ............... 55/434; 73/28.04, 28.06, 863.21, 863.22, 863.23
See application file for complete search history.

(56) References Cited

U.S. PATENT DOCUMENTS

| | | | |
|---|---|---|---|
| 2,932,394 | A | 4/1960 | McGinn |
| 3,901,798 | A | 8/1975 | Peterson |
| 4,301,002 | A | 11/1981 | Loo |
| 4,383,171 | A | 5/1983 | Sinha |
| 4,670,135 | A | 6/1987 | Marple |
| 4,767,524 | A | 8/1988 | Yeh |
| 5,183,481 | A | 2/1993 | Felder |
| 5,270,542 | A | 12/1993 | McMurry |
| 5,425,802 | A | 6/1995 | Burton |
| 5,498,271 | A * | 3/1996 | Marple et al. .............. 55/321 |

(Continued)

OTHER PUBLICATIONS

Peng et al. (1995) Generating particle beams of controlled dimensions and divergence: II. Experimental evaluation of particle motion in aerodynamic lenses and nozzle expansions. Aerosol Sci Technol 22:293-313.

(Continued)

*Primary Examiner*—Robert A Hopkins
(74) *Attorney, Agent, or Firm*—Lambert Patent Services; K Karel Lambert

(57) ABSTRACT

A skimmer device for concentrating an aerosol from a flowing gas stream, having an inlet with inlet aperture and inlet raceway, an outlet with virtual impact void and collector channel, and bulk flow divertors symmetrically disposed on either side of the long axis of flow, further characterized in that the downstream walls of the bulk flow divertors are concavedly curved and reverse the direction of bulk flow. In section, the four channels or passages of the "skimmer" thus form a "crossed tee" with concavedly contoured lateral arms curving back around. The lateral flow channels are for diverting the bulk flow into exhaust chimney spaces, and the chimney spaces are positioned proximate to the inlet element and anterior to the collection channel. In operation, the bulk flow streamlines are thereby folded more than 90 degrees away from the long axis of flow on the laterally disposed concave walls of the bulk flow channels. While counterintuitive, this was found using computational fluid dynamics (CFD) and experimentation to dramatically reduce wall separation and related instabilities and to improve particle recoveries. Large two-dimensional arrays of closely stacked inlet and skimmer elements are thus achieved by fitting the chimneys into spaces between parallel inlet elements. The interlinked problems of flow instability, manufacturability of arrays, and scale-up of chimney cross-sectional area to equalize pressure differentials in the bulk flow diverter exhaust ducts, particularly in two-dimensional arrays at high throughput, are uniquely solved with this geometry.

26 Claims, 12 Drawing Sheets (Continued)

U.S. PATENT DOCUMENTS

| | | |
|---|---|---|
| 5,533,406 A | 7/1996 | Geise |
| 5,565,677 A | 10/1996 | Wexler et al. |
| 5,788,741 A | 8/1998 | Burton |
| 6,062,392 A | 5/2000 | Birmingham |
| 6,120,573 A | 9/2000 | Call |
| 6,290,065 B1 | 9/2001 | Kenning |
| 6,386,015 B1 | 5/2002 | Rader |
| 6,402,817 B1 | 6/2002 | Bergman |
| 6,695,146 B2 | 2/2004 | Call |
| 6,698,592 B2 | 3/2004 | Kenning |
| 7,325,465 B2 | 2/2008 | Solomon |
| 2004/0232052 A1 | 11/2004 | Call |
| 2007/0048186 A1 | 3/2007 | Call |
| 2008/0022853 A1 | 1/2008 | Ariessohn |

OTHER PUBLICATIONS

Loo BW et al. Dichotomous virtual impactors for large scale monitoring of airborne particulate matter, In (BYH Liu, ed) Fine Particles: Aerosol generation, measurement, sampling and analysis (1976) pp. 312-349.

Chen, BT and HC Yeh (1985) A Novel Virtual Impactor: Calibration and Use, J Aerosol Sci 16: 343-354.

Novick VS and JL Alvarex (1987) Design of a multi-stage virtual impactor, Aerosol Sci Tech 6:63-70.

Loo BW and CP Cork (1988) Development of high efficiency virtual impactors, Aeros Sci Techn 9:167-176.

Marple VA et al (1980) Virtual Impactors: a theoretical study, Environ Sci Tech 14:976.

Goo, J (2002) Numerical simulation of aerosol concentration at atmospheric pressure by a cascade of aerodynamic slit lenses, J Aerosol Sci 33:1493-1507.

\* cited by examiner

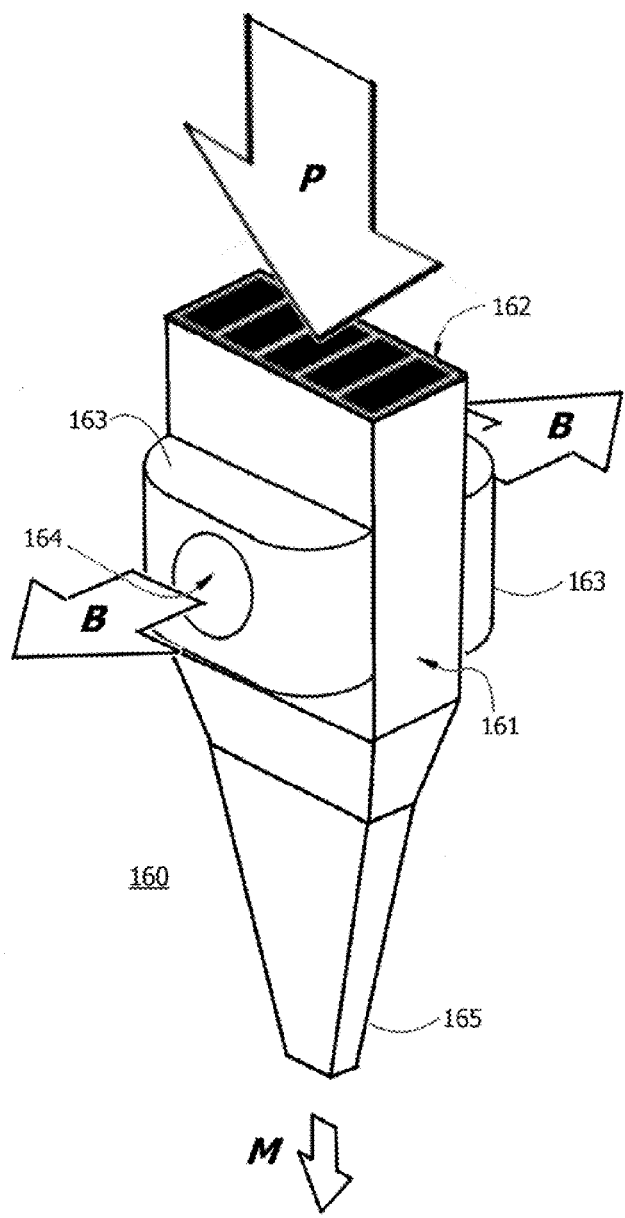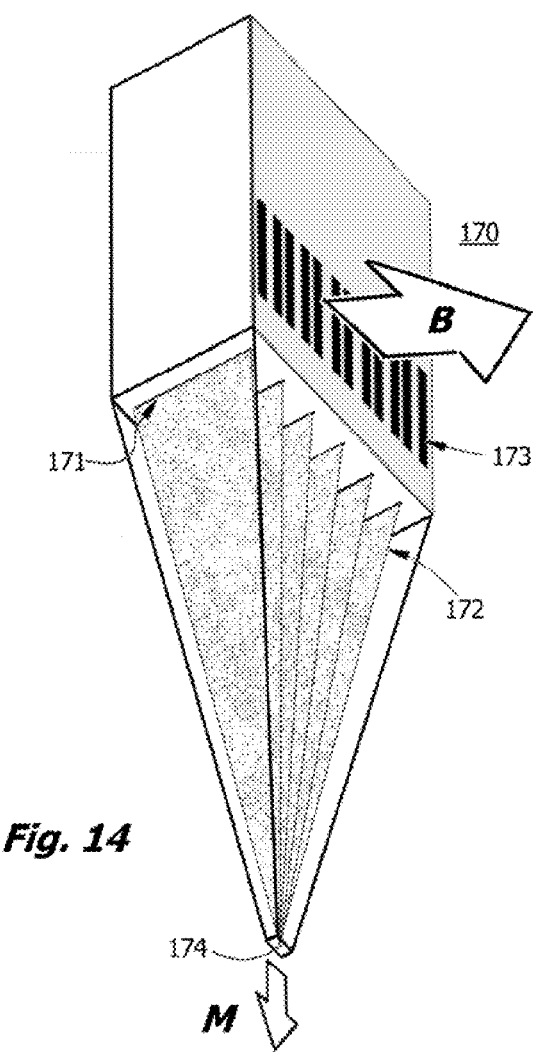
Fig. 13
Fig. 14

SKIMMER FOR CONCENTRATING AN AEROSOL

FIELD OF THE INVENTION

This invention pertains to concentration of aerosol particles or airborne agents in a virtual impactor, and more particularly to a scaleable means for fractionating a focused particle beam into particle-depleted sheath or "bulk" flow and a particle-enriched core or "minor" flow by diverting the bulk flow in an improved "skimmer", and finds use in preparation and testing of aerosol samples [US Class 95/32].

BACKGROUND TO THE INVENTION

Atmospheric aerosols from natural, anthropogenic, and industrial sources have long been recognized as a potential threat to human health. This threat is now compounded by the need to detect and avert acts of terrorism where an infectious or toxic material is deployed in the form of an aerosol. Particles that present the greatest hazard in terms of inhalation and nasal entrapment or lung deposition are respirable particles in the range of 0.02-25 um diameter.

One major challenge that must be addressed by all aerosol samplers is that many aerosols occur at extremely low concentrations, or may be only a small fraction of the urban background aerosol distribution. The aerosol must thus generally be concentrated before sampling. Convergent nozzles and aerodynamic lenses are effective in focusing an aerosol into a beam of particles, a particle-rich core surrounded by a sheath of particle-depleted gas. A discussion of focusing aerosols is found in U.S. Pat. No. 5,565,677 to Wexler and in Peng et al. (1995) Aerosol Sci Technol 22:293-313. But used in isolation such focusing devices are not effective in fractionating the particle-rich core from the particle-depleted sheath flow.

For concentration of particles, a device which may be used in conjunction with nozzles or aerodynamic lenses is a "virtual impactor," which separates particles from carrier gas on the basis of momentum and aerodynamic size [See Loo et al. Dichotomous virtual impactors for large scale monitoring of airborne particulate matter, In (B Y H Liu, ed) Fine Particles: Aerosol generation, measurement, sampling and analysis (1976) pp 312-349]. A virtual impactor does not trap particles by physical impaction, as in plate impactors or impingers, but instead fractionates a particle beam according to a "cut size" characteristic of the virtual impactor, fractionating the gas stream into flows that are termed by convention, the "bulk flow", which is the particle-depleted sheath flow, and the "minor flow", which is the particle-rich core flow of the focused gas stream. Both bulk and minor flows generally flow in the direction of a suction pressure applied to the concentrator. Particles in the minor flow are concentrated in the virtual impactor and remain suspended in a reduced volume of flowing gas. The bulk flow is routed to an exhaust manifold. This function has the advantage that virtual impactors can be operated continuously.

In a virtual impactor, the impaction plate or impinger is replaced by a column of lower velocity gas occupying what is termed a "virtual impact void". The particle-rich core of the particle beam collides with this column of lower velocity gas. The bulk or sheath flow is diverted around it. Historically, this is accomplished by inserting a tubular, wedge-shaped, or conical "collection nose" (also termed a "collection probe") into the flow of the gas stream. The collection nose is commonly acutely tapered at the tip to split off and deflect the sheath flow, and is formed with a tubular channel down its center axis. The mouth of that channel is the virtual impact void. Particles continue through the virtual impact void and are carried in the lower velocity gas stream (the "minor flow") down the channel in the nose (conventionally termed the "minor flow channel" but termed here the "collector"). The coarse particles, with greater inertia, pass into the collector, and in contrast, the sheath flow and some finer particles follow the streamlines of the bulk air flow and are diverted by the outer surface of the nose. In this way, the gas flow is fractionated; the bulk of the gas is diverted away from the nose, and a lesser, particle-rich fraction is concentrated in the collector flow. Because the nose of these virtual impactors generally comes to a sharp tip, it is typically manufactured by machining, or is sacrificially truncated.

Representative virtual impactors are found in U.S. Pat. Nos. 3,901,798, 4,301,002, 4,670,135, 4,767,524, 5,425,802, 5,533,406, 5,788,741, 6,062,392, 6,386,015, and 6,402,817. Because typical virtual impactors do not actually collect particles themselves, but merely redirect them into two different fluid streams according to their mass, they are essentially free of the problems of particle bounce and re-entrainment associated with actual impactor devices. Related designs are described in Chen, B T and H C Yeh (1985) A Novel Virtual Impactor: Calibration and Use, J Aerosol Sci 16: 343-354; in Novick V S and J L Alvarez (1987) Design of a multi-stage virtual impactor, Aerosol Sci Tech 6:63-70; in Loo B W and C P Cork (1988) Development of high efficiency virtual impactors, Aeros Sci Techn 9:167-176; in Marple V A et al (1980) Virtual Impactors: a theoretical study, Environ Sci Tech 14:976; and in Goo, J (2002) Numerical simulation of aerosol concentration at atmospheric pressure by a cascade of aerodynamic slit lenses, J Aerosol Sci 33:1493-1507. As is the case with solid body impactors, parameters used to characterize the performance of virtual impactors include collection efficiency, separation efficiency, wall loss, volume per unit time, flow split, or concentration ratio. A preferred virtual impactor should have a steep cutoff curve and little wall loss, and is preferentially operated at a larger mass transfer rate and flow split.

Typically a virtual impactor is described as having a specific "cut size". This term refers to the particle size above which a given particle has sufficient momentum to cross deflected streamlines and flow into the collector. In contrast, particles smaller than the cut size and carrier gas molecules follow their respective streamlines. By convention, the cut size is determined by measuring the particle size at which 50 percent of the particles of that particular size flow into a collection tube and 50 percent of the particles of that size follow the deflected streamlines. The "efficiency" of a virtual impactor for a particular particle size is the percentage or ratio of correctly fractionated particles over the total number of particles in the sampled gas stream. Efficiency values for different particle sizes are not only indicative of the cut size value, but can also indicate the overall effectiveness of the virtual impactor for other particle sizes. The "particle loss" for a virtual impactor represents the percentage of particles that enter but do not exit the device, and instead adhere to some internal structure, such as the acceleration nozzle, the collection probe inlet, or walls of the collector.

Peterson, in U.S. Pat. No. 3,901,798, claims improvements in reduction in wall loss by stacking two plates, the first plate and the second plate having concentrically located orifices, with a tubular collection nose inserted into the gas flow in the plane of the second orifice so that an annular passage for diversion of the bulk flow (B) is formed around the tubular nose. Minor flow (M) exits at the long center axis. The virtual impactor in this early design is not preceded by a focusing nozzle. This early design of a virtual impactor, represented here in FIG. 1, is not readily scaleable for handling large air flows in a compact device and is expected to have a relatively high cutoff size.

Loo, in U.S. Pat. No. 4,301,002 describes a focusing nozzle and collection probe of a virtual impactor, shown here in FIG. 2. A single air pump provides suction for the device, which measures 45 to 115 cm in height. The tubulation upstream of the virtual impactor (1), in combination with the pendant conical flow acceleration nozzle (termed a "jet orifice," 2) immediately above the conical nose (3) of the virtual impactor, is taught to focus a particle rich core flow (M) and divert the bulk flow (B) around the conical nose. The orifice diameter of the jet orifice is slightly larger than the orifice diameter of the virtual impact void inlet, reducing wall losses. Distance (S) separates the pendant cone (2) of the acceleration nozzle from the conical nose (3) of the virtual impactor. Loo teaches that the impact void nose should be radiused (R) and tapered to smooth separation of the flow streamlines in the separation region. Filters are used to trap particles in the outlet stream. This geometry, however, is associated with stagnation points and eddy instability at the point of flow separation that leads to particle loss by wall collisions and diversion with the bulk flow.

Marple, in U.S. Pat. No. 4,670,135 (FIG. 3) addresses the problem of scaling virtual impactors for higher gas flow sampling rates. In this device, multiple virtual impactors, operated in parallel, and consisting of pendant acceleration nozzles (4) and tubular receiving noses or probes (5), are assembled into larger manifolds. Again, filters are used to collect particles in the bulk (B) and minor flow (M) streams.

Burton (FIG. 4), in U.S. Pat. No. 5,425,802 and U.S. Pat. No. 5,788,741, describes a now familiar construction of acceleration nozzle and conical collection nose (6) with axial virtual impact void. Two vacuum sources are used, allowing the investigator to vary the ratio of the suction pressure applied to the bulk (B) and minor flow (M) channels. However, difficulties are reported due to impaction losses on the cone of the collection probe and to eddying around the virtual impact void.

Kenning in U.S. Pat. No. 6,290,065 describes in (FIG. 5) a virtual impactor with tapered inlet nozzle (7,8), central minor flow passage (collector 9), outlet for collecting a minor flow (M), and lateral flow channels (13) for diverting a bulk flow. Several modules 11 are shown in a one-dimensional row (10). The lateral channels terminate in "major flow ports" on the plane of the paper (12).

A related device is shown in FIG. 6. Minor flow (M) and bulk flow (B) are separated at a virtual impactor (16) formed of "fin-shaped projections" (24), inner walls (26), and minor flow channel (30), the combination forming a virtual impactor body (33). According to Kenning, the invention excludes or is not inclusive of two-dimensional stacks of these sort of devices. Kenning reports, "By improving the particle separation efficiency of each of virtual impactors (16), the present invention allows for employing only one layer or row of virtual impactors (16) for completing particle separation, which eliminates the chances of particles getting lost onto surfaces of additional layers or rows of virtual impactors" (Col 6, lines 1-7 of U.S. Pat. No. 6,290,065). Construction of these devices, particularly the acute angles of the nose, relies on difficult and expensive micromachining techniques.

Similarly, Birmingham, in U.S. Pat. No. 6,062,392, describes separation plates containing linear arrays of acceleration nozzles and "fin-shaped" virtual impactor noses. Importantly, the sharply convex shape of the collection nose is taught to reduce wall losses in this design. Birmingham teaches, "The virtual impactor is generally haystack-shaped and includes a convex leading surface. The convex surface faces the outlet end of the nozzle. The convex surface includes a virtual impact void therethrough. The virtual impact void defines a terminal end of a minor flow channel that extends through the separation plate to the second surface." (Col 3, lines 58-63). And further that a "dead fluid" zone or a zone of stagnant air is created adjacent to the convex surfaces surrounding the virtual impact void, the convex surfaces permitting improved collection of the minor flow (Col 6, lines 18-25). This description is consistent with wall separation, which is accompanied by instability in the flow regime around the nose, and is not expected to result in higher efficiencies at higher flow rates and flow splits.

Bulk flow is diverted to ducts interposed between the minor flow channels and from there out through orifices in the coverplates of the device. These separation plates, however, cannot be stacked because of mechanical interferences, and because pipeflow resistances rapidly lead to a decrease in pressure drop in the bulk flow exhaust from one layer to the next. According to Birmingham, "By improving the particle separation efficiency of each of virtual impactors 16, the present invention allows for employing only one layer or row of virtual impactors 16 for completing particle separation, which eliminates the chances of particles getting lost onto surfaces of additional layers or rows of virtual impactors" (Col 6, lines 38-42). Construction of these devices also relies on difficult and expensive micromachining techniques.

In contrast to the single-layered devices of Birmingham and Kenning, Ariessohn's "Aerodynamic Lens Particle Separator" (US 20080022853), describes an expandable two-dimensional array of micro-aerodynamic lenses for focusing large volumes of moving air into concentrated particle beams. FIG. 7 is a conceptual model used for illustration of a virtual impactor and skimmer used in conjunction with an upstream aerodynamic lens. Bulk flow (B) in the ADL-skimmer element is directed into lateral flow channels perpendicular to the long axis of flow of the gas stream in the accelerator nozzle, shown here in section with aerodynamic lens ringlets (34) adorning the throat of the skimmer. See also FIG. 8 of the published application. US 20080022853 is co-assigned and is herein incorporated in full by reference.

Arrays of the devices of FIG. 7, like those of Birmingham and Kenning, are not readily assembled by joining individual modules. In multiple layers, the lateral flow channels would necessarily be connected in series, increasing resistance with depth of the array, and resulting in degraded performance. Also, there is no provision for combining collector flows downstream from multiple devices in an array.

Related art is described by Goo (Goo J. 2002. Numerical simulation of aerosol concentration at atmospheric pressure by a cascade of aerodynamic slit lenses. J Aerosol Sci 33:1493-1507). FIG. 8 of the reference describes computer modeled streamline flow in a skimmer having orthogonally directed lateral flow channels. Eddies in the throat of the skimmer arms impinge on the long axis of flow of the particle beam. Also seen is wall separation in the streamlines branching laterally. When similar geometries are tested experimentally, particle capture efficiency decreases are noted, due to loss of particles to the bulk flow and due to collision of particles with the walls around the mouth of the virtual impactor.

Thus, there is a need in the art, for a virtual impactor module that overcomes the above disadvantages, is readily manufactured without recourse to micromachining, and can be scaled or assembled in arrays to accommodate larger flow throughputs at high ratios of bulk flow to minor flow.

SUMMARY OF THE INVENTION

The present invention provides a compact skimmer for efficiently separating an aerosol-rich minor flow from a focused gas stream. The skimmer is generally paired with an aerodynamic lens, convergent nozzle, or other upstream intake member. For higher throughput, paired nozzle and skimmer or aerodynamic lens (ADL) and skimmer units (nozzle:skimmer and ADL:skimmer pairs) are assembled into arrays containing a plurality of such unit pairs. The concentrator arrays may be linear arrays or two-dimensional arrays for processing large volumes of gas. Palisaded arrays may be wrapped around a cylindrical tubular housing or disposed on some other hollow surface. Advantageously, when packed in palisaded arrays, the chimney structures required for operation of the skimmers may be compactly folded between adjoining intake members and ducted to a common exhaust manifold. Adaptor manifolds for pooling the minor flows of very large collector arrays are also disclosed. Miniaturized arrays of this kind could be manufactured by micromachining, but may advantageously also be manufactured using injection molding.

The body of the inventive skimmer is generally bounded by a top surface and a bottom surface separated by a distance "H" and has an inlet end and an outlet end. Between the enclosing upper and lower bounding surfaces, the body of the skimmer includes two frontend body members of height "H" separated by a inlet channel having an "inlet aperture" for receiving a gas stream. The upstream aspects of the frontend skimmer body members form an inlet aperture therebetween and the centerfacing walls of the frontend body members form a channel termed the "inlet raceway" for receiving the gas stream into the skimmer body and accelerating the particle beam.

In a preferred embodiment, the inlet end of the skimmer is fluidly connected to an outlet end of an aerodynamic lens, convergent nozzle, other intake member, or a combination thereof. The inlet raceway defines the long axis of flow of the gas stream, and is generally coaxial (or coplanar) with the flow of the gas stream in a combination device having an upstream aerodynamic lens, nozzle, or other intake member.

The body of the skimmer also includes two downstream body members of height "H" separated by a collector channel for conveying a minor flow stream. The collector channel is formed by symmetrically opposed inner walls of the downstream skimmer body members and is coaxial (or co-planar) with the long axis of flow of the gas stream. The inlet of the collector channel as defined by the proximate upstream aspects of the two outlet body members is the "virtual impactor void". In one embodiment, the collector channel height H may be tapered, with a maximum at the inlet and a minimum at the collector outlet, thereby forming a funnel for shaping a ribbon of flow into a more symmetric stream.

Within the body of the skimmer are two lateral flow channels in fluidic communication with the gas stream. The union of the lateral flow channels, the inlet raceway, and the collector channel forms a "crossed-tee" junction, and the virtual impact void is the mouth of the collector channel. The lateral flow channels bear sharply away from the long axis of flow and separate the frontend body members and the backend body members. The lateral flow channels are generally symmetrical and are formed between the downstream or "posterior" walls of the frontend body members and the upstream or "anterior" walls of the backend body members. Each of the lateral flow channels is characterized in that the upstream walls of the downstream body members (i.e. facing the lateral flow channels) are generally concavedly curved or contoured, that is, the lateral arms form a path for the bulk flow streamlines curve in an arc that is generally orthogonally or obtusely bending away from long axis of flow through the crossed tee junction, albeit 'curvedly bending away' and not perpendicular or straight walled. It can be said that the virtual impactor void is centered on a "concavedly curved" solid impactor surface. This is done to coherently port the bulk flow away from the minor flow by arcuately bending it more than 90 degrees, even more preferably more than 110 degrees, even more preferably more than 150 degrees, and most preferably about 180 degrees from the long axis direction of flow. It can be said that the throat of the device is configured to bend the bulk flow along an arcuate path away from the direction of the long axis of flow, the arcuate path bending more than 90°, in another embodiment more than 110°, and in another embodiment about 180° from the long axis of flow. In one embodiment, effectively, the bulk flow is directed into a "U-turn". This leads to a more compact collector device and improves the collection efficiency by eliminating or reducing flow instability, wall separation, and stagnation zones around the virtual impact void and the throats of the lateral flow channels.

Configured this way, the lateral flow channels open into "chimney spaces" disposed contralaterally on either side of the inlet body members, thereby forming an enlarged exhaust duct for the bulk flow. The chimney spaces or "shafts" are generally perpendicular to the body of the skimmer but not requiredly so. When directed orthogonally and/or perpendicularly to the body of the skimmer, the chimney shafts form an outlet port extending through at least one enclosing surface of the skimmer body, the top, the bottom, a side plate, the other side plate, or a combination of top and bottom or side and side.

The skimmer bodies of the present invention can therefore be advantageously stacked or arrayed. In this aspect of the present invention, two dimensional arrays of nozzles (or aerodynamic lenses) and skimmers are provided. Plural nozzle: skimmer or ADL:skimmer combinations (stacked pairs) are arrayed in palisading rows and rows are stacked upon rows. Chimneys extend through the stack between the nozzle elements and are joined to convey the bulk flow to a common exhaust manifold. Preferably, all the collector channels are joined in a common adaptor manifold, or funnel-like element, and the enriched particle fraction from each of the skimmers is pooled for collection or further processing.

In a preferred embodiment, the chimneys and outlet ports lie between the inlet members of a palisaded linear array of concentrators. In a yet more preferred embodiment, the chimney and outlet ports penetrate multiple layers of a two-dimensional stack of linear arrays, forming a common outlet ductwork joined to an exhaust manifold, which in turn is fitted with a means for generating a suction pressure, such as a vacuum pump, blower, or other vacuum source. In practice, the flow resistance in each of the bulk flow channels and collector channels will establish the flow split of the device when operated with a common source of suction pressure source.

The generally concave upstream walls of the backend skimmer body members, also termed the downstream walls of the lateral flow channels, the chimney spaces, the outlet orifices, and the exhaust manifold, are configured for extracting a bulk flow from the focused particle beam or ribbon under conditions where the bulk flow remains generally coherent and laminar, even at high flow rates and flow splits.

In operation of a two-dimensional array of nozzle (aerodynamic lens, or other intake member) and skimmer element combinations, particle-laden gas streams are first caused to enter the inlet, generally under suction. The gas streams are accelerated and focused into a particle beam or ribbon as they enter the inlet raceway of the skimmer bodies and advance toward the virtual impact void between the concave surfaces of the backend body members. The minor flow continues into the collector channel; it exits the collector channel downstream and can be collected or processed further. The bulk flow, depleted of particles according to the efficiency of the virtual impactor, is diverted into the lateral flow channels, where it is supported on concavedly contoured surfaces, thereby increasing coherence of the flow. The bulk flow is conveyed to the chimney structure and enters the exhaust ducts. Accordingly, each element of the two-dimensional array separates a particle beam into a minor flow exiting a downstream face of the array and a bulk flow exiting a lateral face (or faces) of the array. Linear arrays (rows) of concentrator elements operate similarly. Both linear and sheet arrays may be manufactured by stacking individual modules or by forming multiple units of intake member:skimmer pairs simultaneously.

It has been said here that the lateral flow channels of the inventive skimmers are characterized in that the upstream walls of the downstream body members are generally concavedly curved or contoured, that is, the lateral arms of the flow channels curve in an arc that is generally orthogonally or obtusely bending away from long axis of flow through the crossed tee junction. In another sense, the throat of the lateral flow channels is concavo-convexedly curved, and bends back so as to intersect a line drawn through the crossed-tee junction perpendicular to the long axis of flow, in some instances forming a "U-turn". In one embodiment, the streamlines can be contoured in an arcuate path bending concavedly away from the long axis of flow and then recontoured so as to bend back in an "S" shape. In some skimmers, the throat of the lateral flow channels can be a diverging throat, in others a converging throat, and so forth.

Uses of the present invention include detection of biological or chemical warfare agents in the form of aerosols, collection of industrial pollutant particles such as fly ash in a gas plume, sampling of air in buildings associated with "sick building" syndrome, collection of infectious or disease-causing organisms in hospitals and public spaces, the collection of radioactive particles, and collection of biological aerosols such as endotoxins, indoor and outdoor allergens, and so forth. It is also contemplated that the present invention may be used for the detection and collection of airborne particles associated with illegal drugs and explosives or their precursors. The concavedly curving lateral channel configuration disclosed here is discovered to be associated with improved particle recovery.

BRIEF DESCRIPTION OF THE DRAWINGS

The teachings of the present invention can be readily understood by considering the following detailed description in conjunction with the accompanying drawings, in which:

FIG. 1 derives from U.S. Pat. No. 3,901,798 to Peterson.

FIG. 2 is a prior art view. FIG. 2 derives from U.S. Pat. No. 4,301,002 to Loo.

FIG. 3 is a prior art view. FIG. 3 derives from U.S. Pat. No. 4,670,135 to Marple.

FIG. 4 is a prior art view. FIG. 4 derives from U.S. Pat. No. 5,788,741 to Burton.

FIG. 5 is a prior art view. FIG. 5 derives from U.S. Pat. No. 6,290,065 to Kenning.

FIG. 6 is a prior art view. FIG. 6 derives from U.S. Pat. No. 6,062,392 to Birmingham.

FIG. 7 is a prior art view. FIG. 7 derives from US 20080022853 to Ariessohn.

FIGS. 13 and 14 are renderings demonstrating the operation of a device for collecting a minor flow using a collector array of five nozzle:skimmer units.

FIG. 20 is a close-up view of streamlines showing wall separation. FIG. 21 is a close up view of 0.8 micron particle tracks showing wall collisions and particle losses into the bulk flow.

FIG. 23 is a close-up view showing coherent streamlines along the downstream wall of the lateral flow channel. Organized large eddies do not impinge on the inlet particle beam. FIG. 24 is a close up view of 0.8 micron particle tracks showing a relative absence of wall collisions or particle losses at the mouth of the virtual impactor, as was confirmed experimentally.

DETAILED DESCRIPTION

Figure 1:
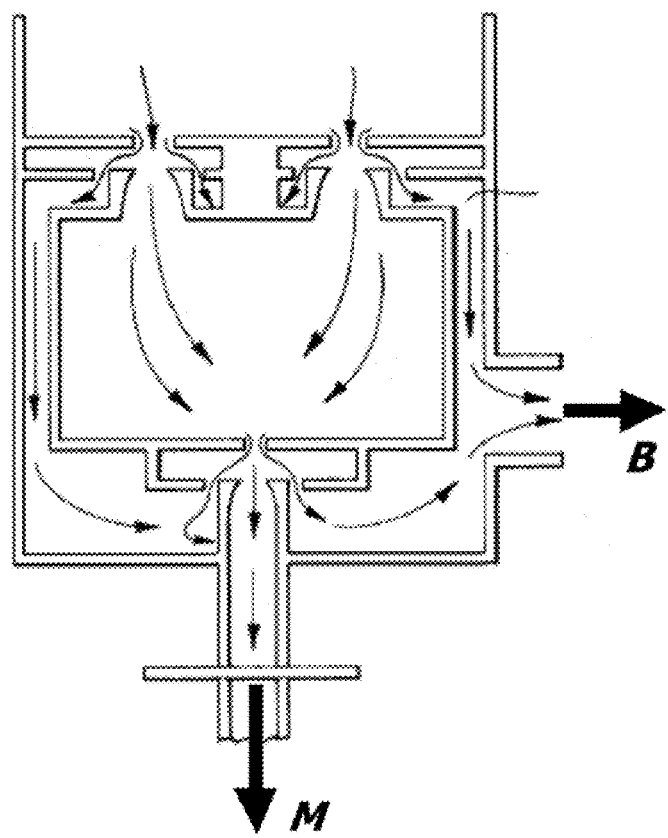
FIGS. 1-7 are prior art sectional views of virtual impactor devices.
Figure 4:
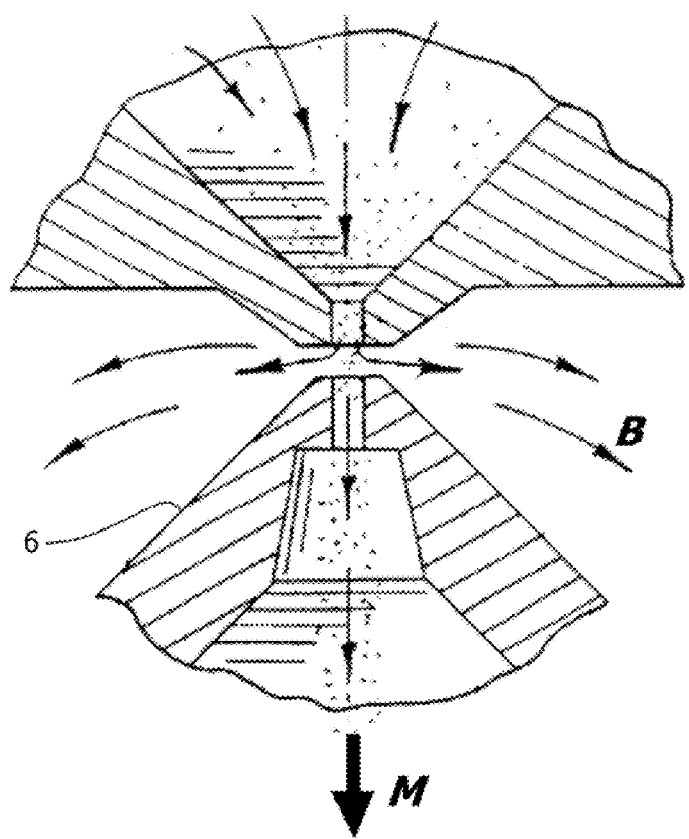
Figure 2:
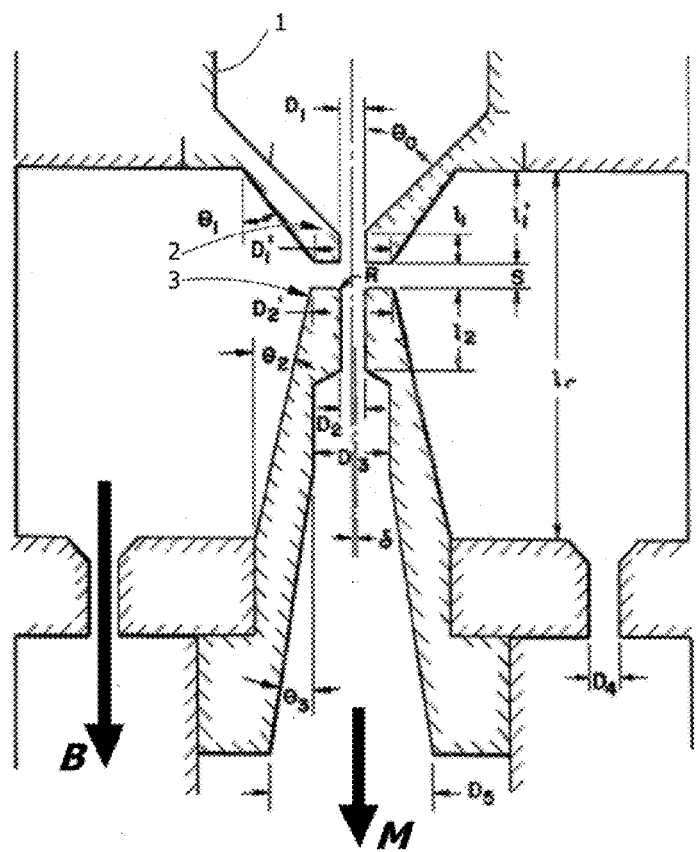
Figure 3:
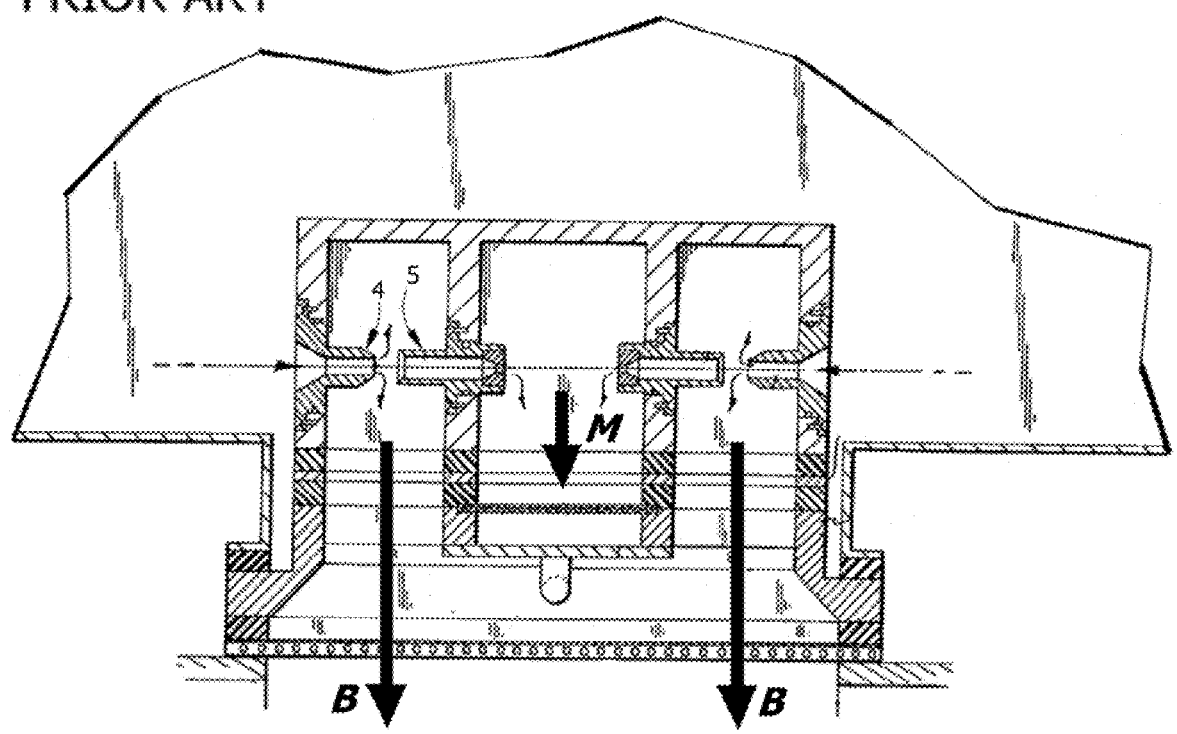
Figure 5:
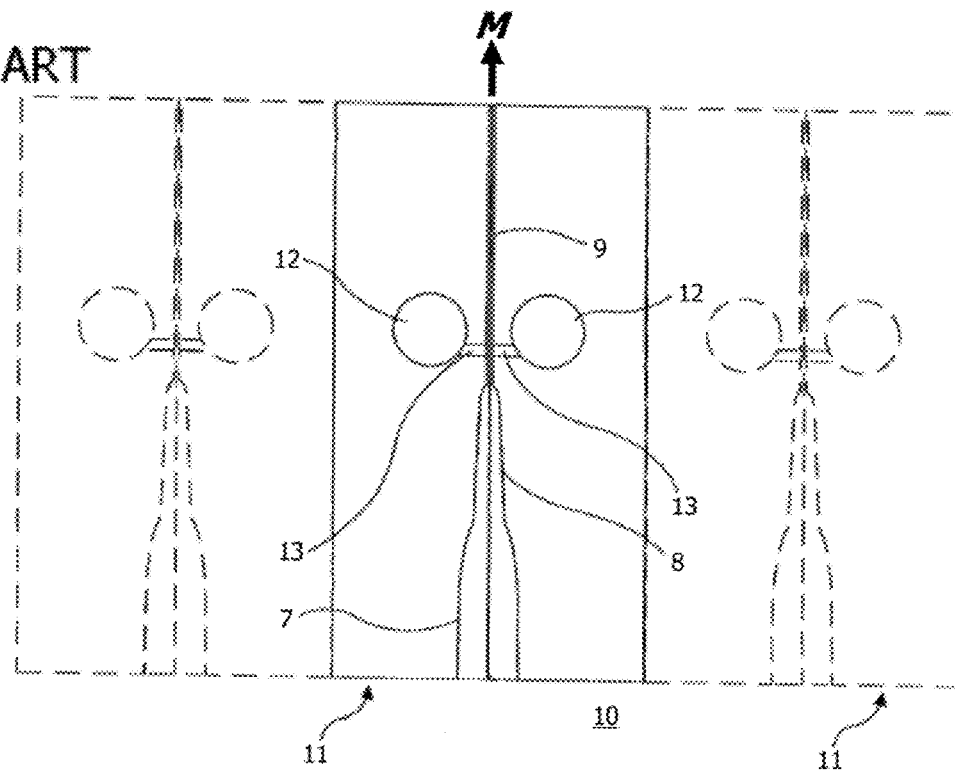
Figure 6:
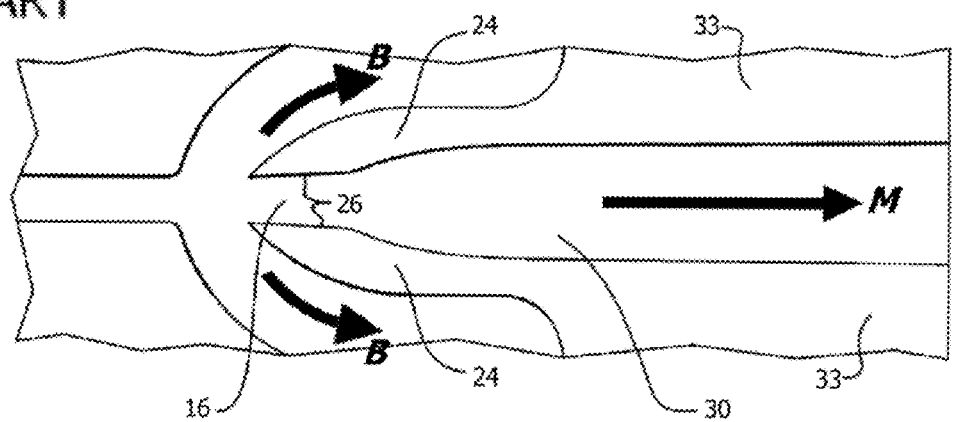
Figure 7:
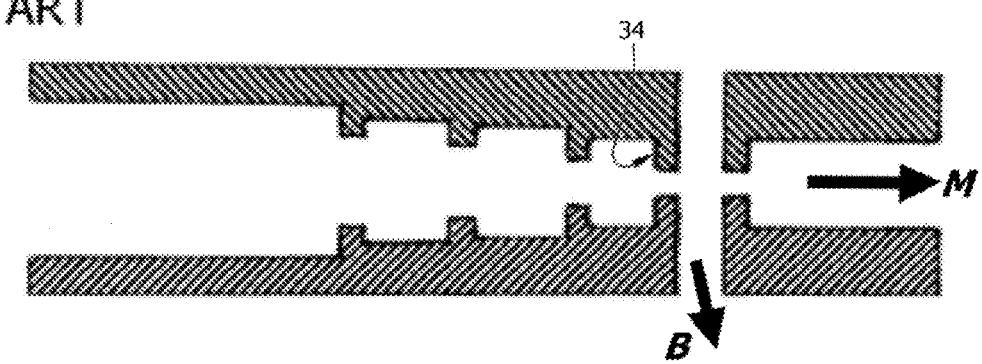

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

Throughout the present description, the terms "upstream" and "downstream" are used to refer to an orientation in respect to the direction of the gas stream flow from the inlet of the device to the outlet of the device on its long axis of flow.

A nozzle or aerodynamic lens, for example, is typically placed upstream of a skimmer. An upstream wall of a lateral flow channel faces the outlet, and so forth. Similarly, "anterior" refers to an aspect or member in proximity to or in the direction of the inlet and "posterior" to an aspect or member in proximity to or in the direction of the outlet.

"Aerosol"—refers to a body or bodies of solid, liquid or gel-like particulate matter suspended in a gas volume, and may connote a population of such particulate bodies. This can include dust motes, exfoliated skin, fibers, spores, vegetative cells, mists, condensates, mucous droplets, microdroplets of saliva and bronchial secretions, pollen grains, bacterial cells, viruses, aerosolized biowarfare dispersions, inorganic particles (road dust or chemicals) and the like. The particulate body may be a composite, containing both solid and liquid matter. Such particulate bodies can remain suspended in a gas for long periods of time, can be carried on currents in the air, or can settle onto surfaces from which they may be resuspended by agitation.

"Minor flow" refers to a particle-rich stream formed by focusing an aerosol and splitting off a particle-depleted "bulk flow". A virtual impactor provides the means for fractionating the minor flow and the bulk flow. The minor flow flows into a "collector channel". The bulk flow flows into "lateral flow channels", or "passages", which are most commonly symmetrically disposed around the long axis of flow of the gas stream and which divert the bulk flow to exhaust.

"Intake element, unit, or manifold", also termed an "intake member", refers to any portal or portal-associated structure for admitting a gas stream (and entrained aerosol particles) into a device or apparatus, generally under the influence of a suction pressure attached to an "outlet" downstream from the inlet. Intake members generally have at least two opposing walls. Intake members include intake manifold, intake orifice, intake port, intake slit, aperture, tube, pipe, channel, tubularity, conduit, duct, passage, mouth, throat, raceway, and the like. A preferred intake member includes focusing elements for forming a particle beam within the gas stream. Focusing elements include inlet raceway, convergent nozzle, acceleration nozzle, tapered nozzle, virtual cyclone, acceleration slit, aerodynamic lens, and the like, as are known in the art.

Figure 24:
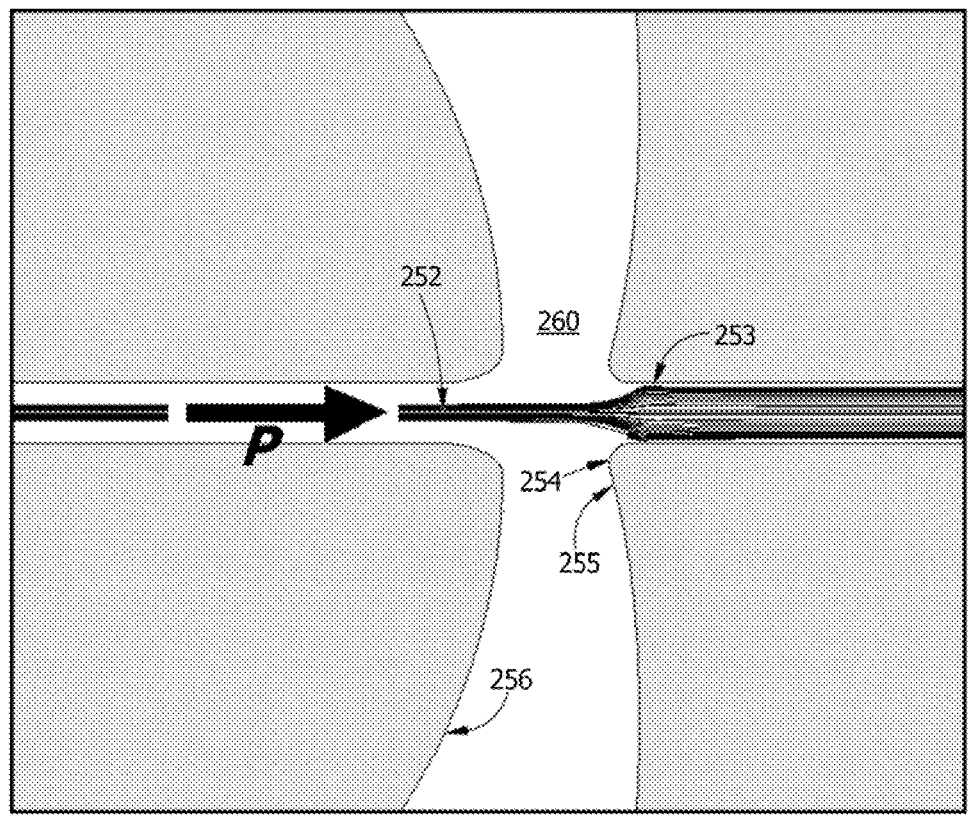

"Concavoconvex": having one concave and one convex surface, as in a bending channel having two opposing walls, where one wall is bent concavedly and the other wall is bent convexedly. The two walls need not be equidistant at all points, and the channel may taper or broaden, for example a throat in the form of a bell, as in the bell of a musical instrument, but of rectangular cross-section. By way of example, FIG. 24 illustrates a throat (260) having concavedly curving downstream wall (255) and convexedly curving upstream wall (256); the throat thus widens concavoconvexedly. However, subsumed within the scope of this definition are concavoconvexedly curving walls that are generally equidistant and concavoconvexedly curving walls that converge or diverge.

Figure 8:
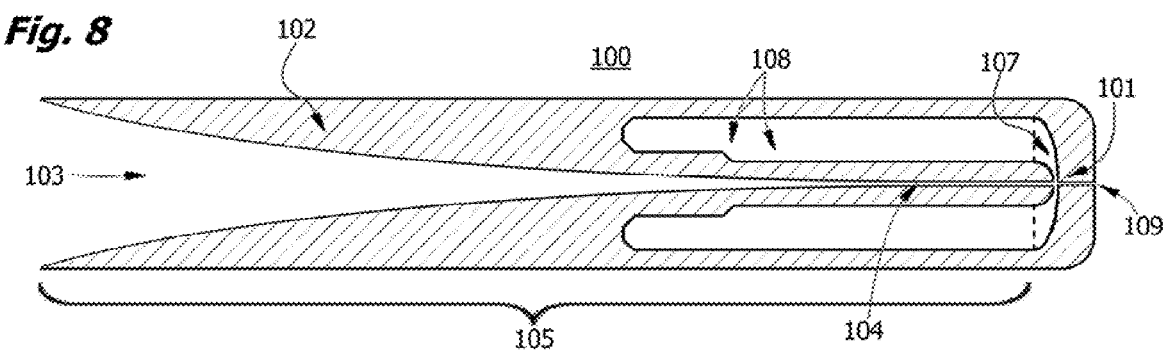
FIG. 8 is a plan view of a device including a combination of a nozzle and a skimmer of the invention.

Turning now to the figures, FIGS. 1-7 are sectional views of prior art virtual impactors supplied here for comparison and discussed above in the introductory remarks. FIG. 8 is a plan view of a device of the present invention, showing a skimmer (101) and tapered nozzle (102) combination in a collector body (100). Not shown in this plan view are cover plates sealing the top and the bottom of the device. A gas stream entering the inlet (103) of the nozzle (from the left) is focused into a particle beam by the tapered surfaces of the nozzle and enters the skimmer body through an inlet raceway (104) as a gas jet. The intake member 105 is a combination of the acceleration nozzle and inlet raceway. The gas stream in the inlet raceway can be considered as a symmetric gas jet with a particle-rich core and a particle-depleted sheath. The particle-depleted sheath is diverted in lateral flow channels (107) to chimneys (108) disposed on either side of the long axis of flow and extending almost half the length of the collector body. The lateral flow channels bend the bulk flow back and away from the direction of flow established in the inlet in a sort of a "u-turn". The chimneys are contoured to fill space in the collector body not occupied by the higher order stages of the nozzle and inlet raceway. The minor flow continues into the collector channel (109) and exits the device on the right.

Figure 9:
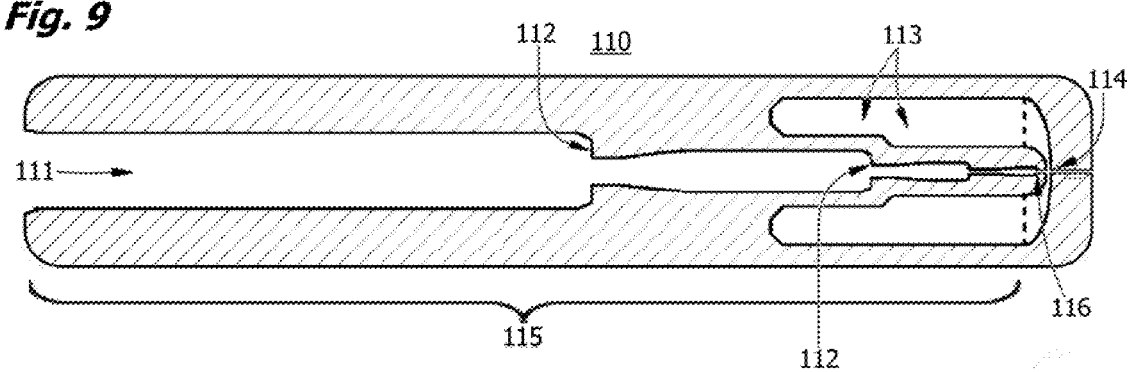
FIG. 9 is a plan view of a device including a combination of an aerodynamic lens and a skimmer of the invention.

FIG. 9 is a plan view of a similar device 110, but the inlet (111) is a composite of multiple aerodynamic lens elements (112). The chimneys (113) are sized in proportion to the flow rate and the flow split, as is discussed further below. Also shown is skimmer (114) with short inlet raceway (116). The intake member 115 is a combination of a nozzle, a series of aerodynamic lenses (112), and the inlet raceway (116).

Figure 10:
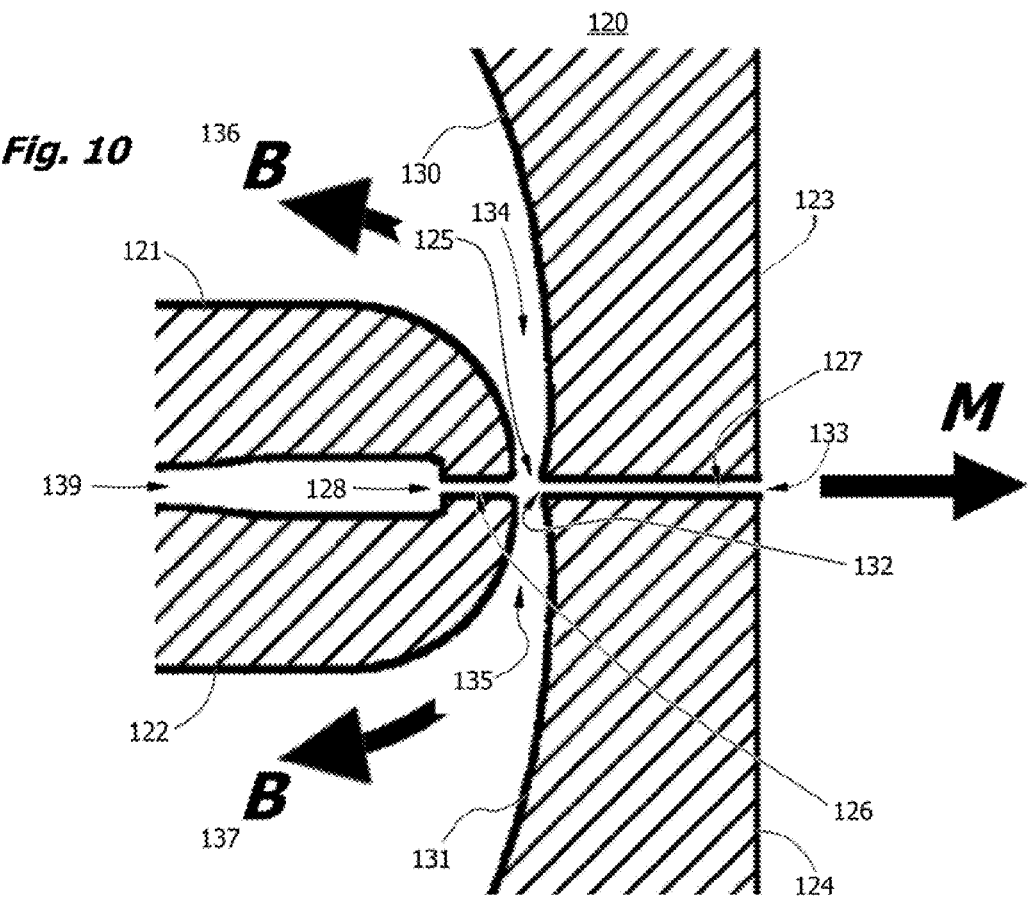
FIG. 10 is a detail of a skimmer body with concavedly arcuate surfaces cooperatively presenting a virtual impact void, the virtual impact void forming the inlet to the collector channel for the minor flow.

FIG. 10 is a detail of a skimmer body (120). The skimmer body can be understood as having four members: two frontend body members (121, 122) and two backend body members (123, 124) forming the corners of a crossed-tee junction (125). Not shown in this sectional view are cover plates or enclosing surfaces sealing the top and bottom of the skimmer body. Between the frontend body members, the particle beam is conveyed through inlet (139), inlet aperture (128), and inlet raceway (126). Between the backend body members, the minor flow stream is conveyed through collector channel (127). The concave anterior surfaces (130, 131) of the backend body members (123, 124) cooperatively present therebetween a virtual impact void (132) to the oncoming gas stream exiting the inlet raceway (126). The virtual impact void forms the mouth or inlet to the collector channel (127). The collector channel terminates in an outlet (133). Contralateral lateral flow channels (134, 135) divert bulk flow to the chimneys (136, 137). In this example, the internal cross-sectional areas of the inlet raceway and the collector channels are equal. But in other embodiments, the collector channel may be fractionally larger or smaller than the inlet raceway channel outlet diameter or dimension.

Also, the flow split to the minor flow collector channel and lateral flow channels can be varied by adjusting the ratio of the parallel resistance to flow in the pathways, for example with valves, choked orifices or other flow restrictions, if this is desired. In a typical application, the ratio of minor flow to bulk flow is 1:10 to 1:400, more preferably 1:20 to 1:200. These resistances are controlled by adjusting cross-sectional areas in the throats of the channels or by adding resistances in series along one or the other of the pathways.

The "inlet aperture" (128) forms the mouth of the inlet raceway (126) and may be a slit, a rectangle, an ellipse, or other geometric shape. In a preferred embodiment, the inlet aperture is a slit and the inlet raceway has a rectangular cross-section with a width of 20-1000 microns, more preferably 50-200 microns and a height scaled to the required flow throughput. Because of the very small dimensions of the channels of the skimmer body, the flow in the channels will be generally laminar (Reynolds numbers <2000, more preferably <1200) and the flow will attain steady state laminar flow, reducing and stabilizing or eliminating stagnation and recirculation zones in the collector channel and skimmer. The inlet raceway, in its broadest embodiment, is simply a narrowing of the inlet passageway, and the inlet aperture is simply the entrance of the inlet passageway into the skimmer body.

The virtual impact void (132) is the inlet to the collector channel (127) and is located symmetrically at the center of flow of the generally concave surfaces formed by the upstream walls of the skimmer outlet body members. The virtual impact void can be a hole or a slit, for example.

Larger cross-sectional areas of the chimneys are enabled by placing the chimneys between adjacent nozzles without increasing the spacing of the nozzles. Because the pressure drops across the mouth of the lateral flow channels and mouth of the collector channel affect performance, narrow or tortuous lateral flow channels, chimneys and exhaust ductwork could result in large and non-uniform pressure drops between skimmer bodies in the center of the array versus the edges of the array, degrading overall performance. A larger cross-sectional area of the chimneys ensures that performance parameters are constant for the entire collector array independent of depth of the array and height of the chimney stack.

Operationally, a gas stream entering the skimmer through inlet (139) is focused into a particle-rich core and a particle-depleted sheath. The gas stream linear velocity is accelerated in the nozzle and aerodynamic lenses, forming a planar jet with particle-rich core. At the "crossed-tee" junction (125) of the inlet raceway (126) and the lateral flow channels (134, 135), the sheath of the gas stream is stripped away by negative pressure in the chimneys and only the core streamlines cross through the virtual impact void (132) at the mouth of the collector channel (127). Particles, by virtue of their aerodynamic size and inertia, continue with the core flow, whereas the particle-depleted sheath streamlines bend and follow the lateral flow channels (134, 135) into the chimneys (136, 137). Bulk flow diverted to the chimneys exits the device through holes cut in the outside of the device (not shown).

Figure 11:
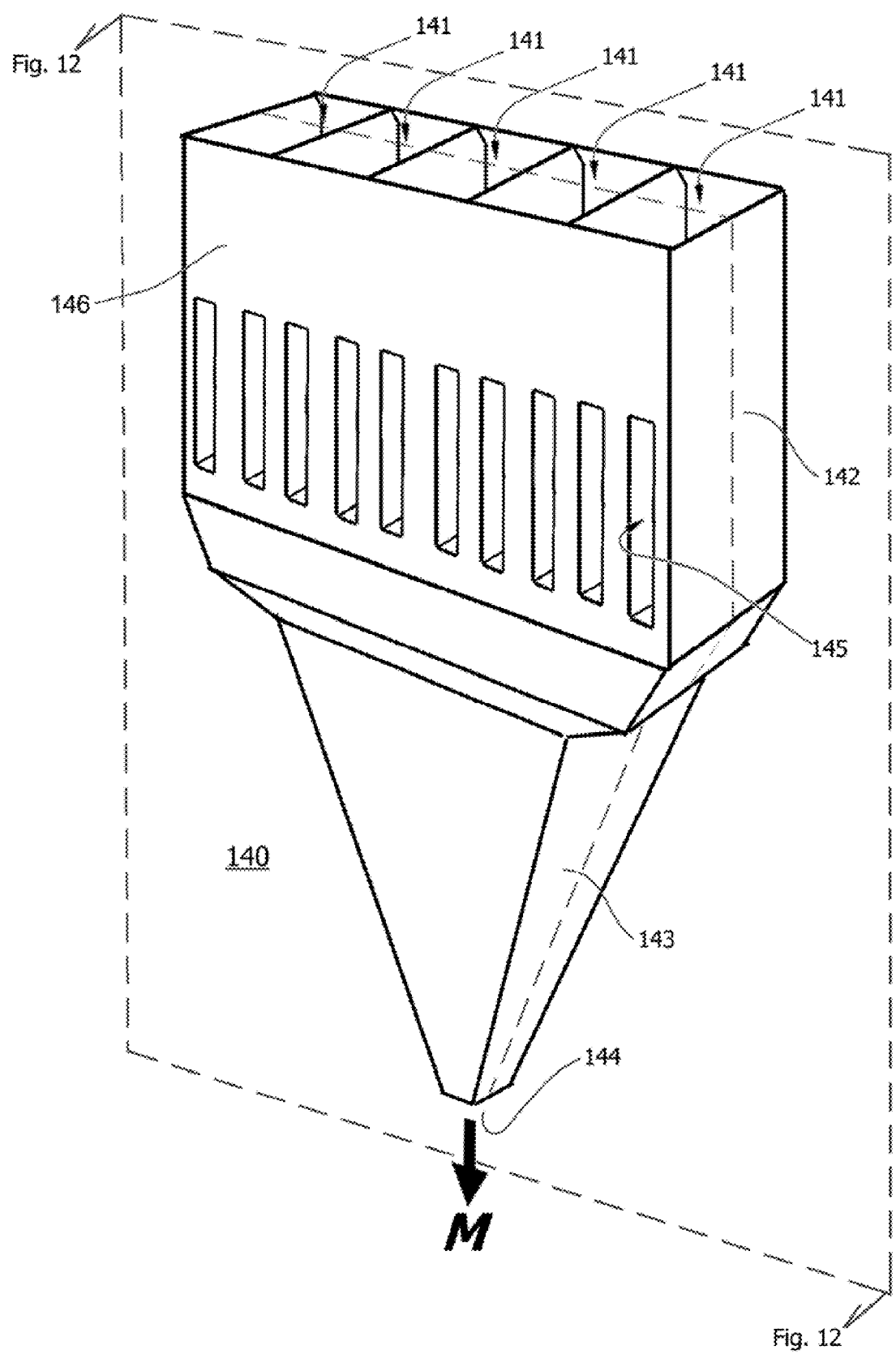
FIG. 11 is a rendering of a linear array of five aerosol concentrators consisting of pairs of aerodynamic lenses and skimmer elements beneath a cover plate. The inlets to the ADL channels are shown at the top, the bulk flow outlets (also termed "chimneys") are shown penetrating the cover plate, and a funnel-shaped downstream transition element (also termed "adaptor") is shown at the bottom. Also marked is the location of the cross-section shown in FIG. 12.

FIG. 11 is a rendering of an array (140) of five pairs of nozzle and skimmer elements (141) in a collector body (142). The inlets of the nozzles are visible on the top of the array. Also shown is a funnel-like adaptor (143) used to pool the minor flows M exiting at the outlet (144) bottom of the array. The exhaust slots (145) on the front of the array are the orifices or "chimney stacks" through which the bulk flow is exhausted from the device. Note that the slots 145 pierce the top cover plate 146 or surface closing the sheath body members. The workings of this device are shown in a sectional view in the following figure. Also shown in FIG. 11 is a cut-line for the sectional view of FIG. 12, where a "y-axis" is defined as perpendicular to the plane of the section as shown.

Figure 12:
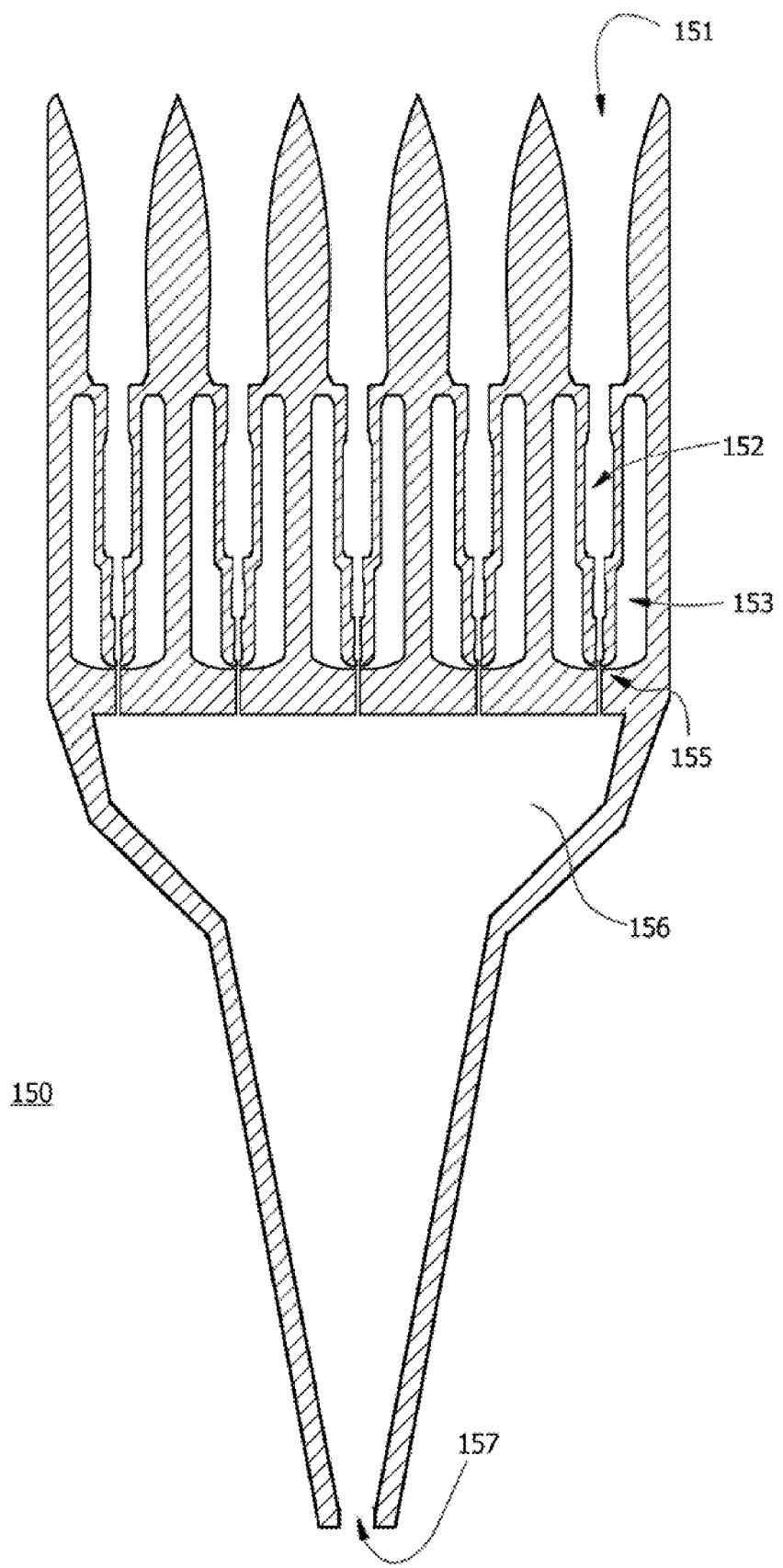
FIG. 12 shows a section through the 5-membered linear array of FIG. 11.

FIG. 12 shows a section through the array of FIG. 11. The five inlets visible in the uppermost surface of the preceding figure can be seen here to be formed by five nozzles (151) and aerodynamic lens elements (152) adjoining each other in a palisaded array. Shared side walls 158 join adjacent intake members. Chimneys (153) honeycomb the walls that form the nozzles and intake. Five skimmer elements (155), operating in parallel, are observed at the base of the five inlets. The adaptor manifold (156) at the base of the device is tapered to direct the minor flow streams exiting the skimmers to a common port (157) for further processing or analysis.

The minor flow streams which exit the aerodynamic lens array may be accelerated in the converging channels of the adaptor, and delivered to another, second-stage aerodynamic lens or nozzle and skimmer, which can provide an additional concentration step.

In FIG. 13, shown is a rendering of an apparatus (160) for collecting an aerosol from inlet stream (P) using the collector array of the preceding figure. The collector array (161) with five inlets (162) is shown with exhaust manifold (163) covering the exhaust slots (145) visible on the front of the array in FIG. 11. An open common exhaust duct (164) is shown on the front of the exhaust manifold (163). In use, gas collected at the upper mouth of the array is accelerated in the upper part of the inlet nozzles and passes through skimmers hidden within the base of the array. Arrows marked "B" show the direction of the bulk flow. A common adaptor (165) forms the base of the array. A single, concentrated minor flow (M) exits at an outlet port or aspect at the bottom of the apparatus.

FIG. 14 shows the underside of a collector-skimmer assembly (170) with six outlet slits (171) and six flow ribbons of particulate rich air (172). The mechanism is essentially as per the collector array of the preceding figure. Gas collected at the mouth of the array is accelerated in the upper part of the array and passes through skimmers hidden within the base of the array. The arrow marked "B" shows the direction of the bulk flow out twelve chimney ports (173). The arrow marked M shows the direction of the minor flow. An adaptor (not shown) or housing covers the base of the array. The six flow ribbons of particles (172) exiting the skimmer are converged in the gradual taper of the adaptor funnel and exit the base of the collector (174) in an essentially focused single beam.

Figure 15:
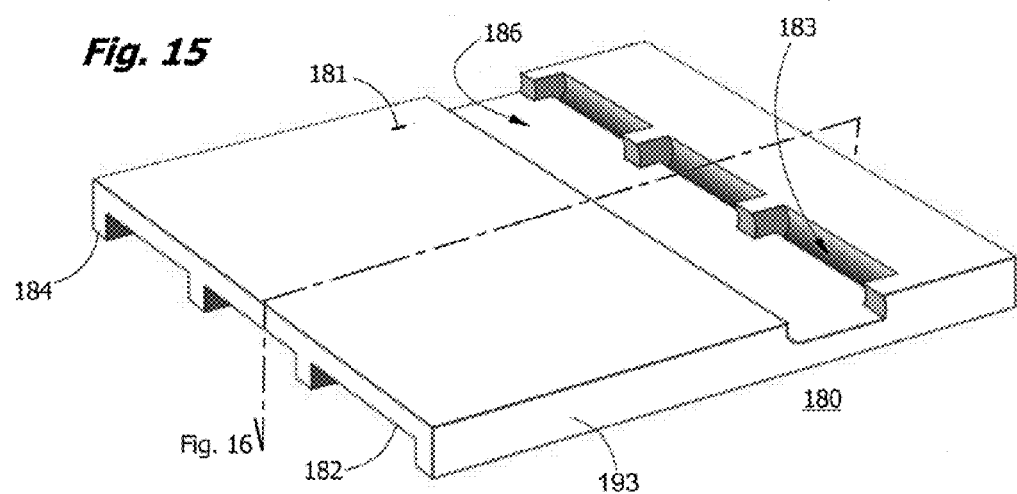
FIG. 15 is a rendering of a first face plate used in the elevational clamshell assembly method. Also shown is the position of the cross-section taken for FIG. 16.
Figure 17:
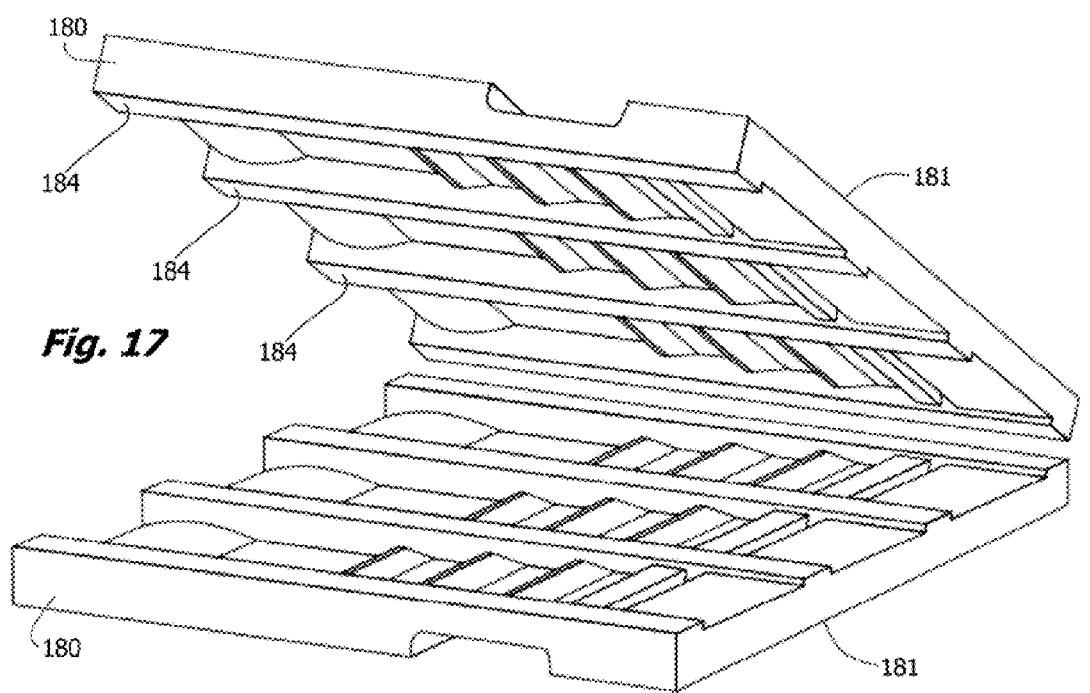
FIG. 17 is an exploded view showing an elevational clamshell manufacturing technique for the collector array of FIG. 5.

Unlike prior art assemblies which are micro-machined, a preferred embodiment of the present invention is made by molding and assembling plastic parts, which can be inexpensively mass-produced. FIG. 15 is an exploded view showing a clamshell manufacturing technique for a collector array with three collectors. A single molded part (180) is used for the assembly. The upper surface of the plate (181), which serves as a side wall or separating plate, is molded with the top halves of the inlet and skimmer elements, including chimney space (186), and the lower surface of the plate (182) is molded with the bottom halves of the inlet and skimmer elements. The lateral flow channels (183) are pierced through the plates. By aligning two plates with opposing faces 181, 182 as shown in FIG. 17, a complete structural unit is obtained. Thin ridges 184 serve as spacers to separate the plates at the proper slit width. The end plates (193) have the dimensions of the ridge separators (184) but serve as sealing plates or members for closing the top and bottom of the skimmer bodies. These end plates have openings for the chimney exhaust flow. Also note that the plates have a plane of symmetry and hence cannot be assembled incorrectly. A single mold may be used to inexpensively form both plates.

Figure 16:
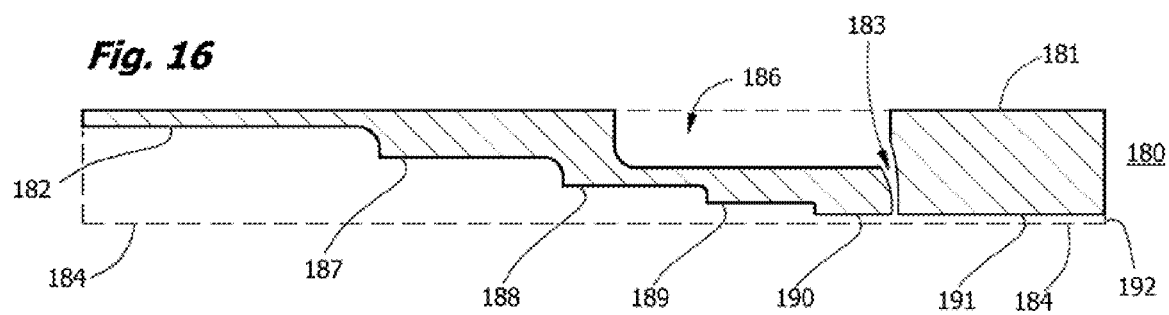
FIG. 16 is a cross-sectional view through the face plate of FIG. 15.

FIG. 16 is a cross-sectional view through a plate, the cut taken as shown in FIG. 15. Shown in bas relief in the upper surface (181) of the plate (180) is the cutout for a partial chimney (186). The channel piercing the plate is a lateral flow channel (183). By stacking the plates so that lower surface 182 of one plate faces the lower surface 182 of a second contacting plate, a fully functional skimmer assembly may be formed (as shown in FIG. 17). By stacking an upper surface 181 of a plate against the upper surface of a second plate, a fully functional chimney is formed. If it is desired to isolate the chimneys of adjacent channels one from the other, an impermeable layer may be inserted between the stacked plates. Also shown on the lower surface (182) are the walls of the inlet nozzle and aerodynamic lens elements (steps 187, 188, and 189 on the lower surface) leading to the aspect forming one inside wall of the raceway (190) and the collector channel (191). The outlet port of the collector channel is formed by the cutaway face at (192). Ridgelike spacers (184, dashed line in section), protruding from the lower surface, separate the channel walls (see FIG. 17) at the proper distance. Male and female registration pins may also be provided in the molded parts to aid in assembly.

Two clamshell configurations are readily conceived. As shown in FIG. 17, a "z-axis" section through the slit in the skimmer results in a clamshell where the two plates are molded to conform to the inside walls of the collector channels and chimneys and the lateral flow channels are pierced through the plates. The z-axis is defined as perpendicular to the plane of the contact interface between the two body members shown in FIG. 17. The opposing plates of the clamshell are separated by the proper distance and supported on spacer ridges (184). The spacer ridges can be glued or ultrasonically welded to seal the units. In an alternate embodiment, a y-axis section (i.e. sectioned as in FIG. 11), in which the clamshell is formed by uniting right and left halves of the skimmer and nozzle body, is also conceived.

Figure 18:
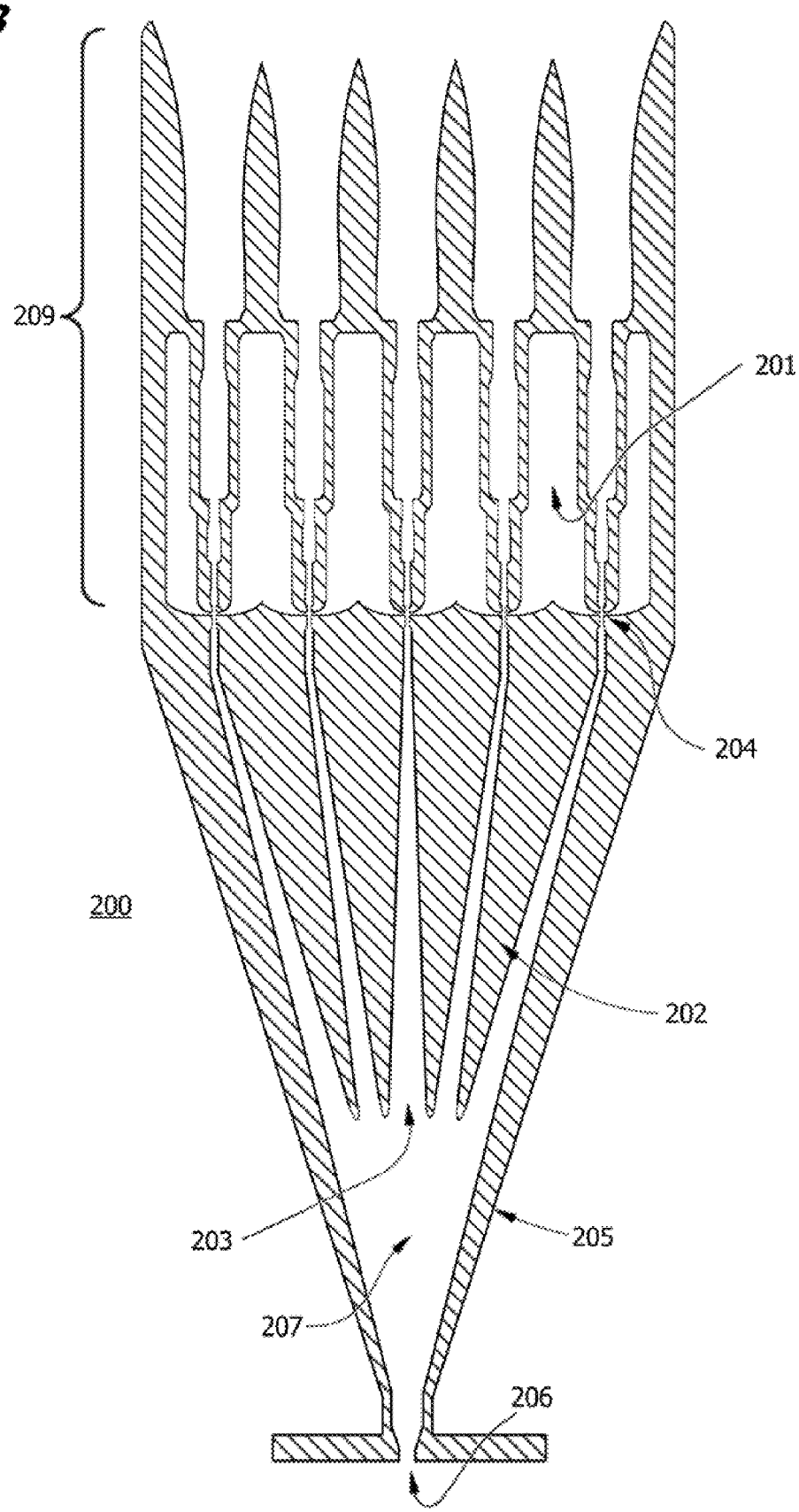
FIG. 18 is an cross-sectional view of a linear array of five nozzle and skimmer elements with wedge-shaped fins extending from the collector outlet ports.

FIG. 18 is a plan view of a linear array (200) of five nozzle and skimmer elements with merged chimneys (201). The elements of the intake member 209 include a palisading array of tapered nozzles and aerodynamic lens elements, herein forming an intake manifold. In the body of the intake member, the honeycomb of chimneys is extensive, further reducing flow resistance in the exhaust ductwork and lightening the mass of the overall device, which in some applications must be portable. Also shown are fins (202) separating the collection channels (203), which are extended into the collection manifold (207) inside the adaptor (205) housing. These serve to maintain velocity in the collection channels so that the particle beams or particle ribbons (172) exiting the skimmer elements (204) can be angled to a common outlet (206) for further processing.

Computational fluid dynamics (CFD) may be used to predict pressure drops and cut size of the devices. Large scale eddy simulation, K-epsilon turbulence calculations, or a full Navier Stokes model may be used. These methods have been used in the design of many of our prototypes over the past few years, many of which have been tested experimentally. Certain hybrid CFD techniques yield relatively good agreement between predictions and actual results without the need to do a full Navier Stokes solution.

Figure 19:
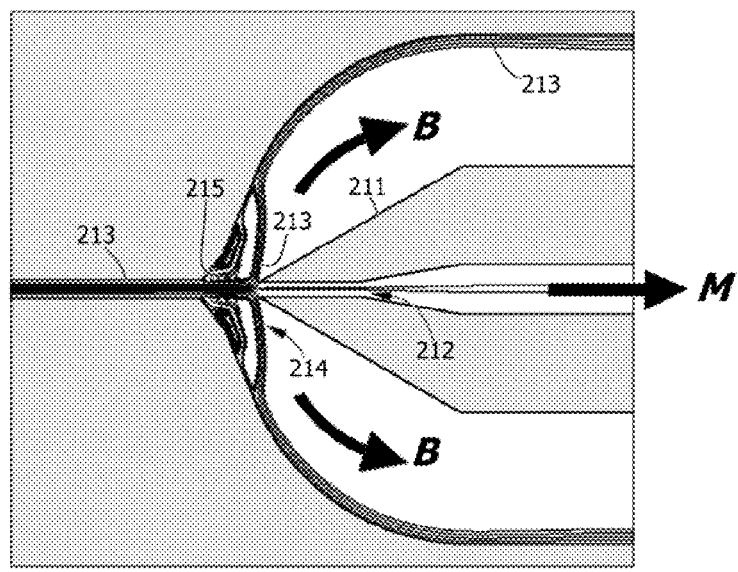
FIGS. 19, 20 and 21 show the results of modeling streamlines and particle tracks (respectively) for a skimmer with sharp-nosed virtual impactor. The design is termed "ADL2".

In FIG. 19, a first CFD result is shown. The solid body represents an early design, designated ADL2, and a wedge-shaped nose (211) with internal collector channel (212) is shown. M and B represent minor flow and bulk flow respectively. Dark lines (213) represent streamlines originating at the inlet. Flow is from left to right. A significant result of this early simulation was the observation of wall separation in the streamlines (214) striking the nose. Significant eddies (215) interacting with the inlet particle stream (213) were also noted.

Figure 20:
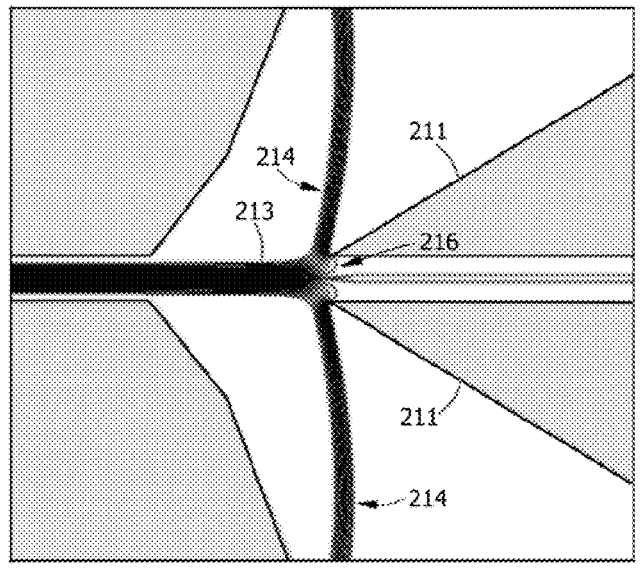
Figure 21:
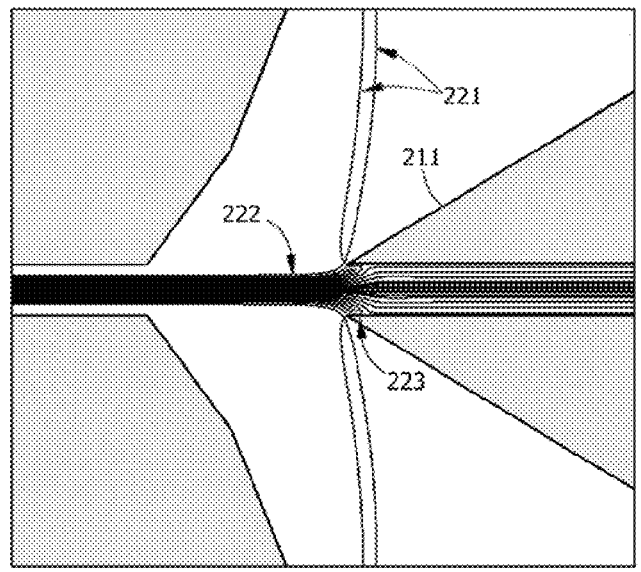

The "wall separation" phenomenon shown in FIG. 20 is striking. Where the particle beam 213 strikes the nose, a major streamline (214) is seen to break away from the outside nose wall (211) in FIG. 20 almost at the tip of the nose. It should be understood that this wall separation conformation is unstable and is associated with traveling vortices or eddies, like the luffing of a sail. Streamlines looping in and back out of the collector channel were also noted (216), as were interactions of the eddies with the particle beam (see 215 above, FIG. 19). As illustrated in FIG. 21, wall separation and chaotic eddies to result in particle loss due to diversion of particles into the bulk flow (lateral particle tracks, 221) and due to wall impact, as can be seen from the particle tracks (222) impacting the walls in the collector channel (at 223).

Figure 22:
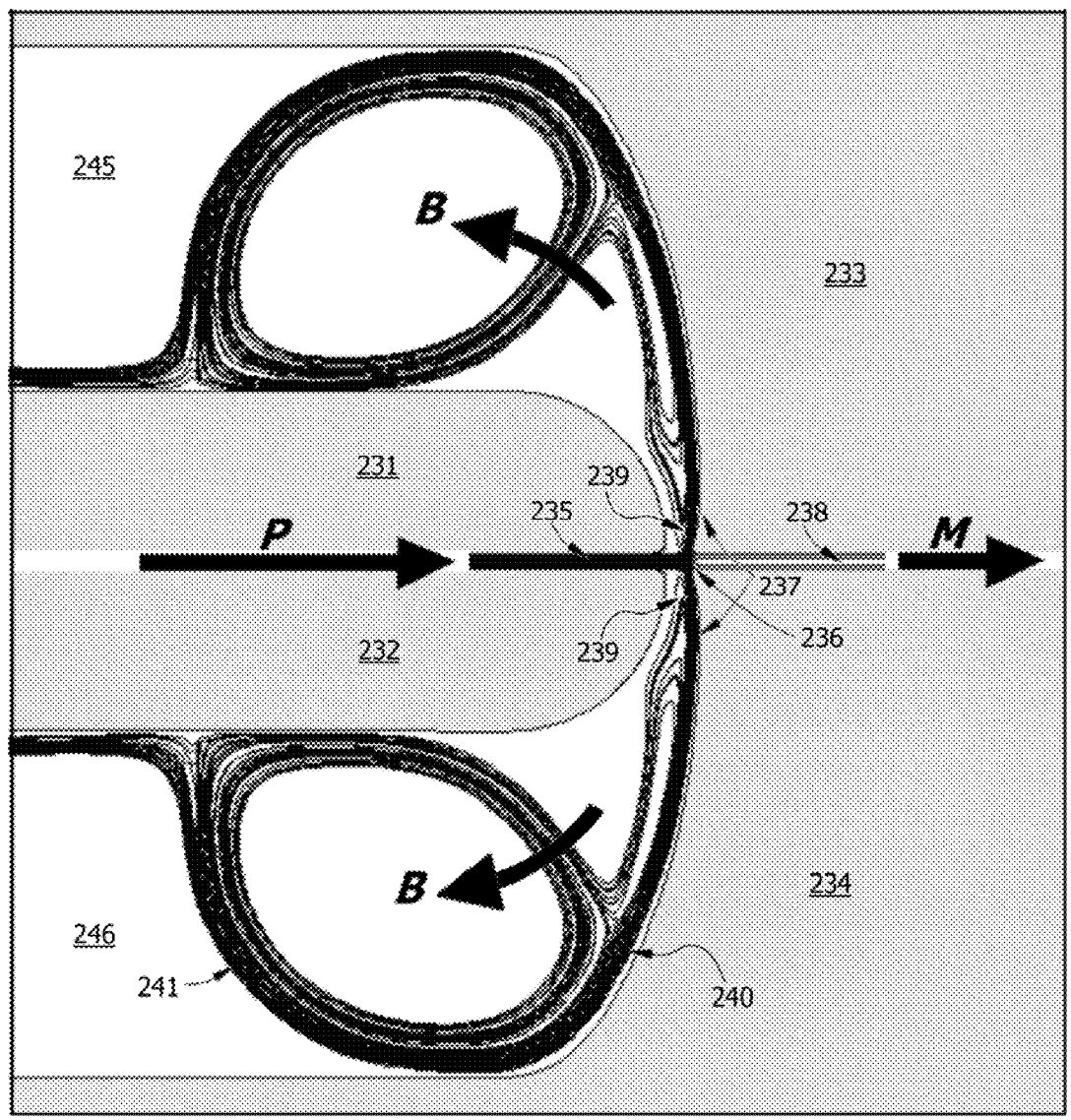
FIGS. 22, 23 and 24 show the results of modeling streamlines and particle tracks (respectively) for a skimmer with blunt, obtuse-angled virtual impactor. The design is termed "ADL408B".

In contrast, the contours of streamlines of ADL408B, shown in FIG. 22, are clearly stabilized by the supporting symmetrical bilateral concave curvature (237, double arrow) of the contoured downstream wall of the lateral flow channels of this model. Here we see the body plan of the skimmer body (230) having four body members in plan section, what can be termed frontend body members (231, 232) and backend body members (233, 234). The anterior walls of the backend body members are concavedly contoured to support the bulk flow streamlines and to bend them more than 90° away from the direction of the long axis of flow, in fact even bending them about 180° from inlet flow direction, a complete u-turn! Note also that in this embodiment, the throat of the lateral flow channels widens progressively from a constriction proximate to the lips of the virtual impact void and flares as it approaches the large chimney cross-sectional voids (245, 246). An aerosol stream P (235) consisting a focused particle beam (or ribbon) and a particle-depleted sheat gas flow, entering the skimmer cross-tee junction (236) is smoothly divided; the particle rich core (238) continuing down the collector channel with the minor flow (M) and the bulk flow (B) coherently turning into the lateral flow arms (239) of the skimmer, where a smaller coherent eddy at 239 is seen to be spatially isolated from the particle beam. Surprisingly, large coherent eddies (240, 241) in the chimneys and lateral flow channels are smooth and stable, and do not impinge on the center axial flow component of the particle beam along the long axis of the collector. There is stability of a major vortex (241) in the chimney. In this embodiment, the vortex propagates vertically up the chimney, which extends as a chimney shaft out of the page. The crossed-tee improvement in the skimmer design with contoured concavedly curving lateral flow arms came as the result of several years of modeling and experimentation. The beneficial impact of this design can be immediately seen in the following table, which was derived by building a physical prototype of the virtual collectors shown in FIGS. 19 (ADL2), 22 (ADL408B) and one having some common features with FIG. 6 (ADL37, not shown), and testing them with particles of known size.

TABLE I

Particle Collection Efficiencies

| | Particle Collection (%) | | | | |
|---|---|---|---|---|---|
| Particle Size (um) | 0.8 | 0.9 | 1.0 | 2.1 | 4.3 |
| ADL2 | 23 | — | 37 | 74 | — |
| ADL37 | — | — | 50 | 50 | 69 |
| ADL408B | 67 | 78 | 81 | 100 | 100 |

These experiments were conducted at a Reynolds number of about 800 and at a flow split of 20:1. Particles tested included polystyrene spheres and *Bacillus subtilis* spores.

As can be seen for ADL408B, the cut size is clearly less than 0.8 microns and collection efficiency of particles greater than 2 microns is 100%. For comparison, recovery data for an earlier prototype of ADL2 (shown in FIG. 19) is also shown. Recoveries were significantly poorer, as was expected from the wall impact predictions of the CFD simulation (FIG. 21). A limited dataset for ADL37, an intermediate prototype with chimneys positioned posterior to the lateral flow channels and "haystack" convexedly contoured walls of a virtual impactor nose, was also not as good. Thus there was a significant and positive benefit achieved by realigning the lateral flow channels to follow a reverse curvature supporting the wall-separating jet (see FIG. 20, 214) noted in the earlier experiments and by positioning the chimney spaces anterior to the lateral flow channels, a benefit not intuitively predictable.

This insight taught us that the streamlines (214) shown in FIG. 20 could essentially be followed in order to configure the reverse contour of the downstream walls of the lateral flow channels. Surprisingly, this path led us to a very counterintuitive design, a design in which the bulk flow is diverted away from the direction of the inlet flow and in fact can be redirected fully 180 degrees from its original direction without particle loss or loss of coherence of the particle beam and sheath flow streamlines. The resulting design discards the characteristic nose or "haystack" teachings of the prior art designs, which are associated with temporal instabilities in the streamlines and wall separation, a problem we found that became worse at higher flow rates and led to reduced particle capture. Wall separation and instable eddies impinging on the particle beam were also seen in our models of skimmers with orthogonally straight-walled lateral flow channels, and these designs were also discarded. A skimmer design represented by ADL408B, with concavedly curving downstream walls of the lateral flow channels, was found to result in superior performance improvements in particle capture and concentration ratio, even at higher flow rates and flow splits.

Figure 23:
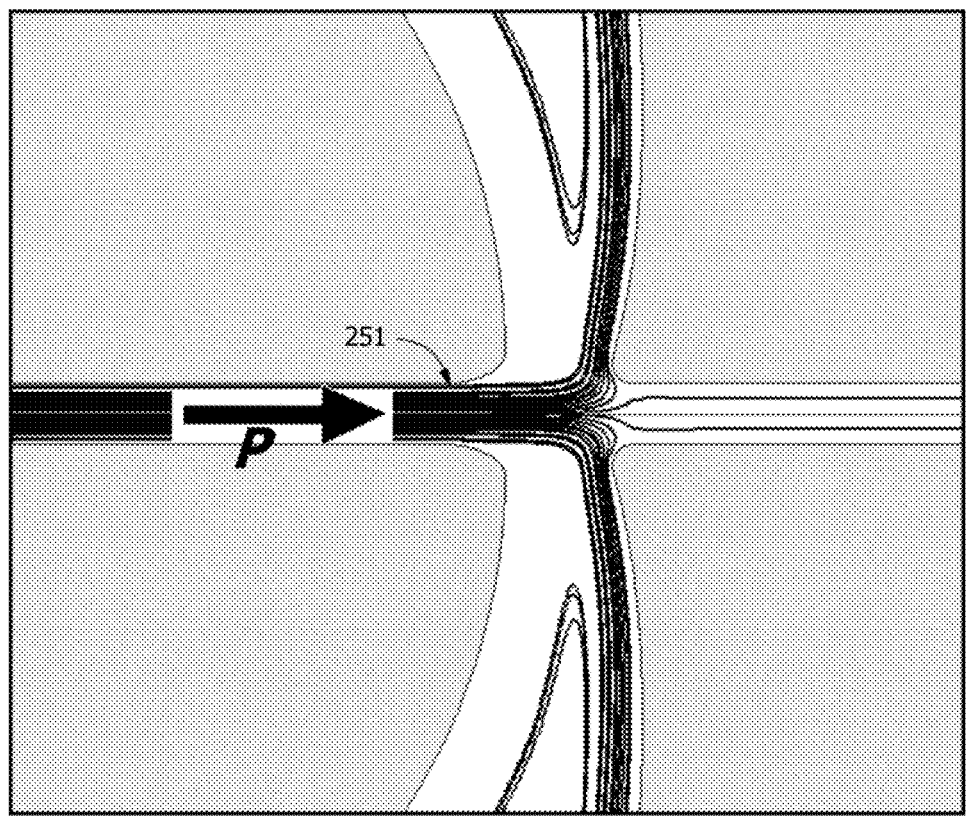

FIG. 23 is a closeup view of a CFD simulation of streamline patterns in the ADL408B design. The particle stream (shown as streamlines 251) entering the skimmer crossed-tee is neatly split into a minor flow and bulk flows moving into the reverse curvature of the lateral flow arms. No chaotic flow is observed near the particle beam.

In FIG. 24, the fate of 0.8 micron particles is studied by virtual simulation. Here a focused particle beam P (shown as "virtual" particle tracks, 252) enters the collector channel with no losses to diversion into the lateral flow channels or wall collision losses at (253). When the corresponding experiment was done in the laboratory, particle capture in the minor flow was 67% (Table I), in reasonably good agreement with the simulation. Note that in this design, the classical teachings of a "tubular probe", a "conical nose", or a "haystack nose", have been discarded and the virtual impact void is a slit at the center of two cylindrically concave surfaces (as in FIG. 10). If viewed in a 3-dimensional embodiment, this would be a bullseye hole in a dish-shaped target, the dish being essentially concavedly curving like the inside of a bowl instead of like the outside of a nose.

Also shown in FIG. 24 is an illustration of a concavoconvexedly curved throat (260), where the downstream wall of the throat (255) is concavedly curved, and the upstream wall of the throat (256) is convexedly curved. In this particular embodiment, the throat has diverging walls, that is to say it flares, so that the throat is narrower at a point near the lips (254) of the center channel and wider at some point further along the length of the throat.

In another aspect, the present invention is an article of manufacture. The product is made by a process in which a one-piece molded part is used to make linear arrays of inlet-skimmer assemblies, each assembly having two interchangeable parts. The piece functions as a right wall of a inlet-skimmer in one orientation and a left wall of the inlet-skimmer in the other orientation. The two halves are assembled with glue or by ultrasonic welding. The pieces can be molded so that the plane of symmetry cuts down the middle of the inlet and collector channel, and the skimmer y-gap dimension or "slit width" is established by spacer ribs on the tops and bottoms of the channels (see FIG. 15-17). Typically these assemblies would be made in strips of multiple inlet-skimmer units. Alternatively, the right and left inlet-skimmer walls can be interdigitated, where one wall projects orthogonally from a support plate, and typically a row of walls are made on a single plate, and then a second plate is flipped over so that the right-facing and left-facing projections interdigitate. By aligning the two plates with registration pins, control of the slit width is readily achieved. Note that in this method, the height of the slit, the z-dimension, is limited by the achievable depth of the mold, whereas in the first example above, the sheets can be made in long strips, the width of the strip determined by the x-axis dimension of the inlet-skimmer design and the length of the strip by the number of units and the height of the slits, i.e. the z-dimension. The height of the slit advantageously can be increased to support an increase in the throughput of the device required for a particular application.

Serendipitously, the concave, generally obtuse geometry of the downstream body members of the skimmer of the present invention is more readily manufactured by injection molding than the acute-angled and convexedly angled nose geometries of the prior art—because the body masses are thick sectioned, unlike the delicate, easily deformed nose geometries of the prior art, which are difficult to manufacture to the required tolerances. Elimination of acute angles in the design associated with prior art designs featuring a "nose" or "tubulated probe" forming the virtual impact void exterior surface and their replacement with the obtuse, radiused, arcuate block design of the ADL408 design, and related designs, clearly relieves potential mass manufacturing problems associated with tight tolerances and thin walls or knife-like edges, another unexpected benefit. Similarly, the devices are easier to manufacture by micromachining, because bends are radiused without the need to form delicate structural features. With this design, lateral flow channel throat constrictions on each side of the virtual impactor void (the mouth of the collector channel, beginning at the lips of the virtual impact void) can be maintained in high-throughput production runs at dimensions in the range of 10-5000 micrometers, depending on the application. For applications such as detection of biowarfare agents, a constriction of 50-255 micrometers can prove useful. For applications such as detection of mining dust, flue gas, or allergens, a constriction of 200-5000 micrometers can prove useful. For applications such as diesel particle exhaust, a constriction of 10-100 micrometers can prove useful.

While the above is a complete description of the preferred embodiments of the present invention, it is possible to use various alternatives, modifications and equivalents. Therefore, the scope of the present invention should be determined not with reference to the above description but should, instead, be determined with reference to the appended claims, along with their full scope of equivalents. The appended claims are not to be interpreted as including means-plus-function limitations, unless such a limitation is explicitly recited in a given claim using the phrase "means for."

Unless the context requires otherwise, throughout the specification and claims which follow, the word "comprise" and variations thereof, such as, "comprises" and "comprising" are to be construed in an open and inclusive sense, as in, "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The invention claimed is:

1. A virtual impactor device for concentrating an aerosol by separating a minor flow from a bulk flow, which comprises:

a) an upstream intake member formed of opposing walls for receiving a gas stream therebetween;

b) a downstream skimmer unit with skimmer unit body, said skimmer unit having an inlet aperture for receiving said gas stream from said intake member, said inlet aperture fluidly conjoined to an inlet raceway, said inlet raceway fluidly conjoined to a junction formed of said inlet raceway, two lateral flow channels and a downstream collector channel, wherein said intake unit, inlet raceway, and downstream collector channel are generally coaxial with the long axis of flow of the gas stream;

c) further wherein said junction divides the skimmer unit body into four body members in plan view, said body members comprising two frontend body members and two backend body members, said two frontend body members forming said inlet raceway therebetween and said two backend body members forming said collector channel therebetween, the upstream mouth of said collector channel forming a virtual impactor void with lips and the downstream aspect of said collector channel forming an outlet from said skimmer body;

d) further wherein a first of said frontend body members and a first of said backend body members form a first lateral flow channel therebetween, said first lateral flow channel having a throat bounded by a posterior wall of said first frontend body member and an anterior wall of said first backend body member, and a second of said frontend body members and a second of said backend body members form a second lateral flow channel therebetween, said second lateral flow channel having a throat bounded by a posterior wall of said second frontend body member and an anterior wall of said second backend body member; said lateral flow channels for receiving said bulk flow; and, e) further characterized in that the anterior walls of the downstream body members curve away from said lips of said virtual impactor void in a generally concavedly contoured bend for contactingly redirecting a major streamline of said bulk flow, and said throat of each said lateral flow channels is configured to bend said bulk flow along an arcuate path away from the direction of the long axis of flow, said arcuate path bending more than 90° away from the direction of the long axis of flow.

2. The device of claim 1, said arcuate path bending more than 110° away from the direction of the long axis of flow.

3. The device of claim 1, said arcuate path bending about 180° away from the direction of the long axis of flow.

4. The device of claim 1, wherein said throat widens concavoconvexedly from a narrower point near the lips of the virtual impactor void to a wider point at a distance along the length of the throat.

5. The device of claim 1, wherein the anterior walls of the backend body members and the posterior walls of the frontend body members are separated at the lips of the virtual impactor void by a constriction in the throat.

6. The device of claim 1, wherein said throat is 20 to 3000 micrometers wide.

7. The device of claim 1, wherein said throat is 200 to 5000 micrometers wide.

8. The device of claim 1, wherein said throat is 50 to 255 micrometers wide.

9. The device of claim 1, wherein said throat is 10 to 100 micrometers wide.

10. The device of claim 1, comprising a means for generating a suction pressure, wherein said means for generating a suction pressure comprises a pump, a blower, a retractable piston, a diaphragm pump, a bellows pump, an eductor, a positive displacement pump, or a vacuum source.

11. The device of claim 10, wherein said means for generating a suction pressure further comprises valves or flow restrictors for independently regulating a flow split across the collector channel and each said throats of the lateral flow channels.

12. The device of claim 1, wherein said intake member is a mouth, a duct, a tubulation, an inlet raceway, an inlet aperture, a convergent nozzle, an acceleration nozzle, a tapered nozzle, a virtual cyclone, an acceleration slit, an aerodynamic lens, a multistage aerodynamic, or combinations thereof, and is configured for forming a particle beam or a particle ribbon in said gas stream.

13. The device of claim 1, wherein said inlet aperture is a slit, and said slit has a rectangular cross-section with a width of 20-1000 microns.

14. The device of claim 1, wherein said inlet aperture is a slit, and said slit has a rectangular cross-section with a width of 50-200 microns.

15. The device of claim 1, wherein said inlet aperture is a slit, and the height of the slit is configured for a particular flow throughput.

16. The device of claim 1, wherein the inlet raceway dimensions and flow rate are configured so that flow is generally laminar and not turbulent.

17. The device of claim 1, wherein the inlet raceway dimensions and flow rate are configured for operation at Reynolds numbers <2000.

18. The device of claim 1, wherein the inlet raceway dimensions and flow rate are configured for operation at Reynolds numbers <1200.

19. The device of claim 1, wherein said skimmer unit body further comprises a sealable top closure and a sealable bottom closure.

20. The device of claim 19, where said sealable top and bottom closures are plate elements.

21. An array comprising a plurality of devices of claim 19, wherein said skimmer bodies are formed in rows so that any two adjacent upstream intake members share a common side wall and said sealable end surfaces are continuous over the top and bottom surfaces of the array, wherein said sealable end surfaces are pierced by a plurality of chimney exhaust shafts.

22. An array comprising a plurality of devices of claim 1, wherein said skimmer bodies are formed in strips so that any two adjacent upstream intake units share a common butt end wall, wherein said common butt end walls are pierced by chimney exhaust shafts (183).

23. A two-dimensional array comprising stacked rows of the arrays of claim 21.

24. A two-dimensional array comprising stacked strips of the arrays of claim 22.

25. The array device of claim 21, 22, 23 or 24, further comprising a common collection manifold with funnel adaptor, said funnel adapted for combining the minor flow stream exiting from said skimmer body outlets of said array.

26. The array device of claim 25, wherein said common collection manifold is configured with internal fins projecting into the common collection manifold, said fins for maintaining velocity and coherence of a particle beam or a particle ribbon exiting each said skimmer body outlet of the array.

* * * * *